United States Patent
Shokat et al.

(10) Patent No.: US 8,278,112 B2
(45) Date of Patent: Oct. 2, 2012

(54) SITE-SPECIFIC INSTALLATION OF METHYL-LYSINE ANALOGUES INTO RECOMBINANT HISTONES

(75) Inventors: Kevan Shokat, San Francisco, CA (US); Matthew D. Simon, Cambridge, MA (US)

(73) Assignee: The Regents of the University of California, Oakland, CA (US)

( * ) Notice: Subject to any disclaimer, the term of this patent is extended or adjusted under 35 U.S.C. 154(b) by 1228 days.

(21) Appl. No.: 11/961,956

(22) Filed: Dec. 20, 2007

(65) Prior Publication Data

US 2008/0199964 A1      Aug. 21, 2008

Related U.S. Application Data

(60) Provisional application No. 60/876,680, filed on Dec. 21, 2006.

(51) Int. Cl.
*G01N 33/00* (2006.01)
*C07K 1/00* (2006.01)
*C07K 14/00* (2006.01)

(52) U.S. Cl. ................. 436/86; 530/358; 530/402

(58) Field of Classification Search ................. None
See application file for complete search history.

(56) References Cited

OTHER PUBLICATIONS

He, S., et al. "Facile synthesis of site-specifically acetylated and methylated histone proteins: Reagents for evaluation of the histone code hypothesis," PNAS, 2003, vol. 100, No. 21, pp. 12033-12038.
Kenyon, G.L., "[40] Novel Sulfhydryl Reagents," Methods Enzymol, 1977, vol. 47 pp. 407-430.
Means, G. E., et al., Reduction Alkylation of Amino Groups in Proteins, Biochemistry, 1968, vol. 7, No. 6, pp. 2192-2201.
Shogren-Knaak, M. et al., "Histone H4-K16 Acetylation Controls Chromatin Structure and Protein Interactions," Science, 2006, vol. 311, pp. 844-847.
Shogren-Knaak, M.A., "[4] Creating Designer Histones by Native Chemical Ligation," Methods in Enzymology, 2004, vol. 375, pp. 62-76.
Shogren-Knaak, M.A., et al., "A Native Peptide Ligation Strategy for Deciphering Nucleosomal Histone Modifications," J. Biol. Chem., 2003, vol. 278, No. 18, pp. 15744-15748.

*Primary Examiner* — Kagnew H Gebreyesus
(74) *Attorney, Agent, or Firm* — Kilpatrick Townsend & Stockton LLP

(57) ABSTRACT

The present invention provides reagents and methods for the introduction of analogues of methyl or acetyl lysine into histone proteins.

23 Claims, 23 Drawing Sheets

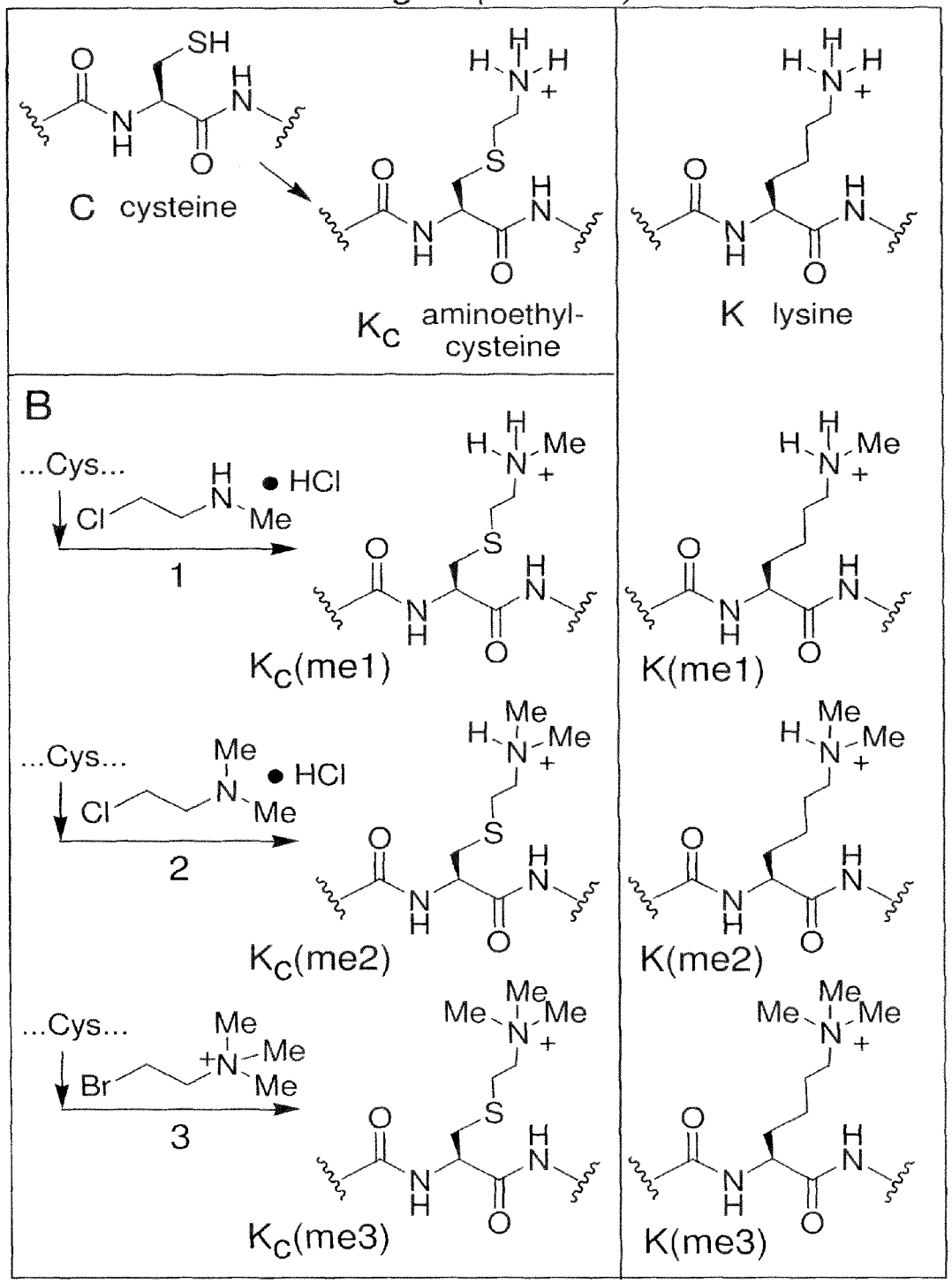
Fig. 1 (sheet 1)

Fig. 1 (sheet 2)
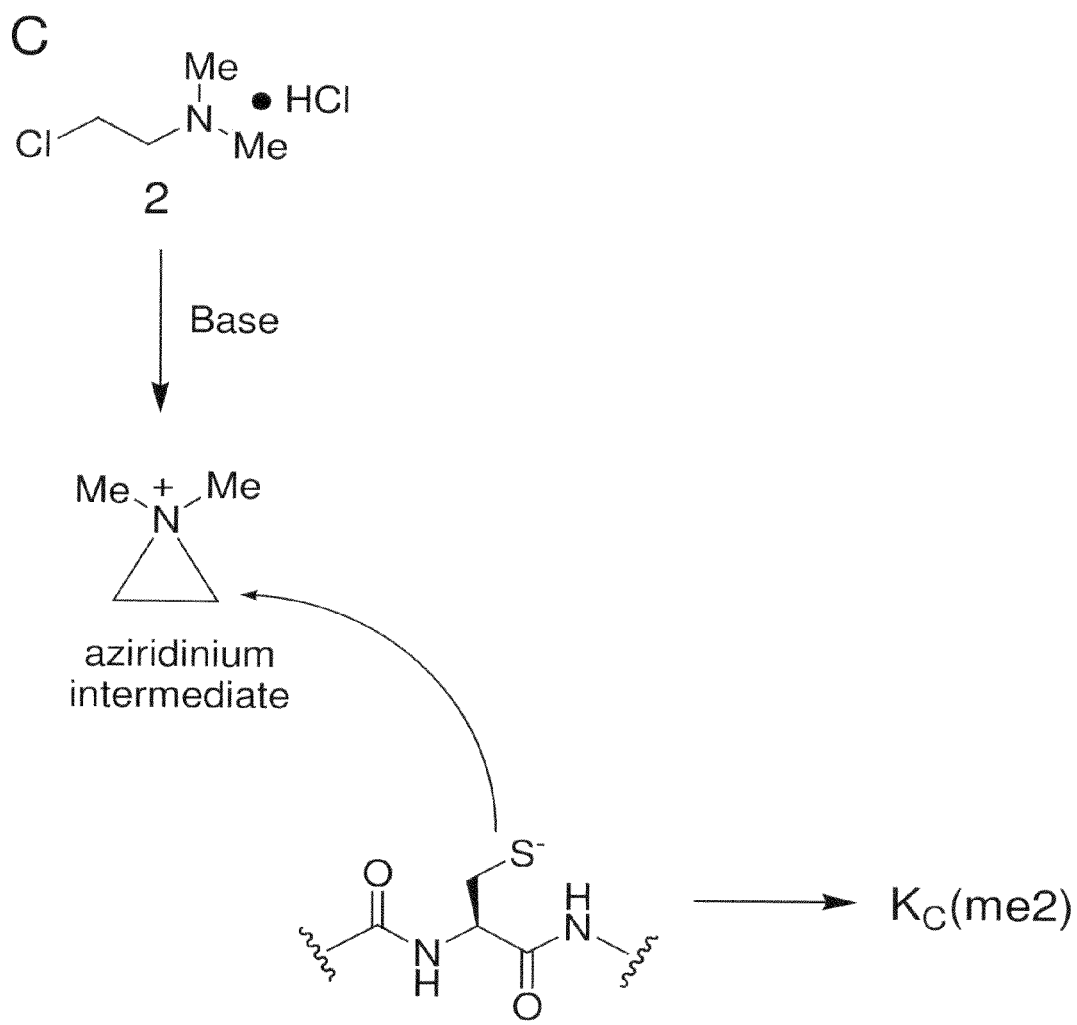

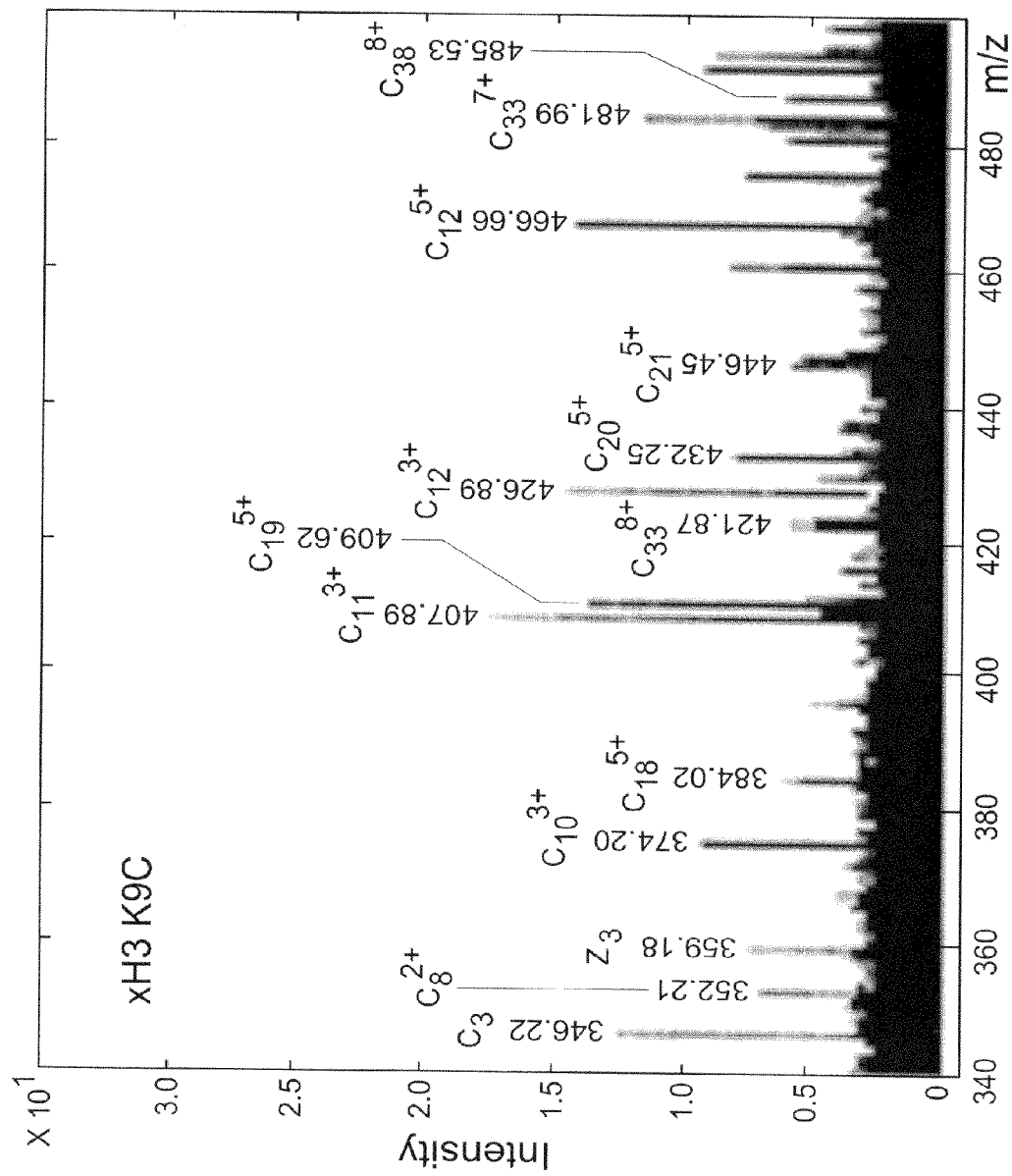
Fig. 2c (sheet 1)

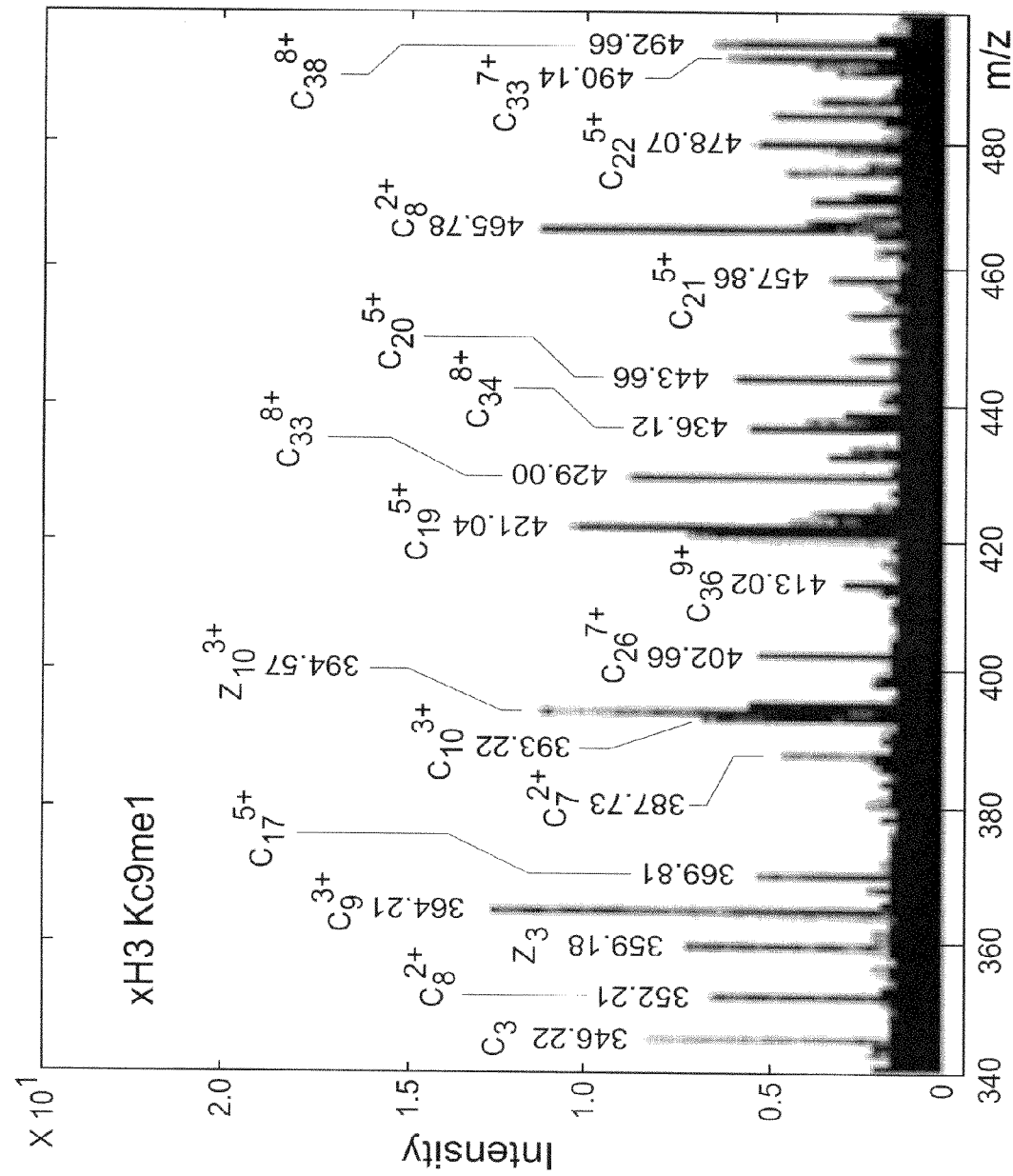
Fig. 2c (sheet 2)

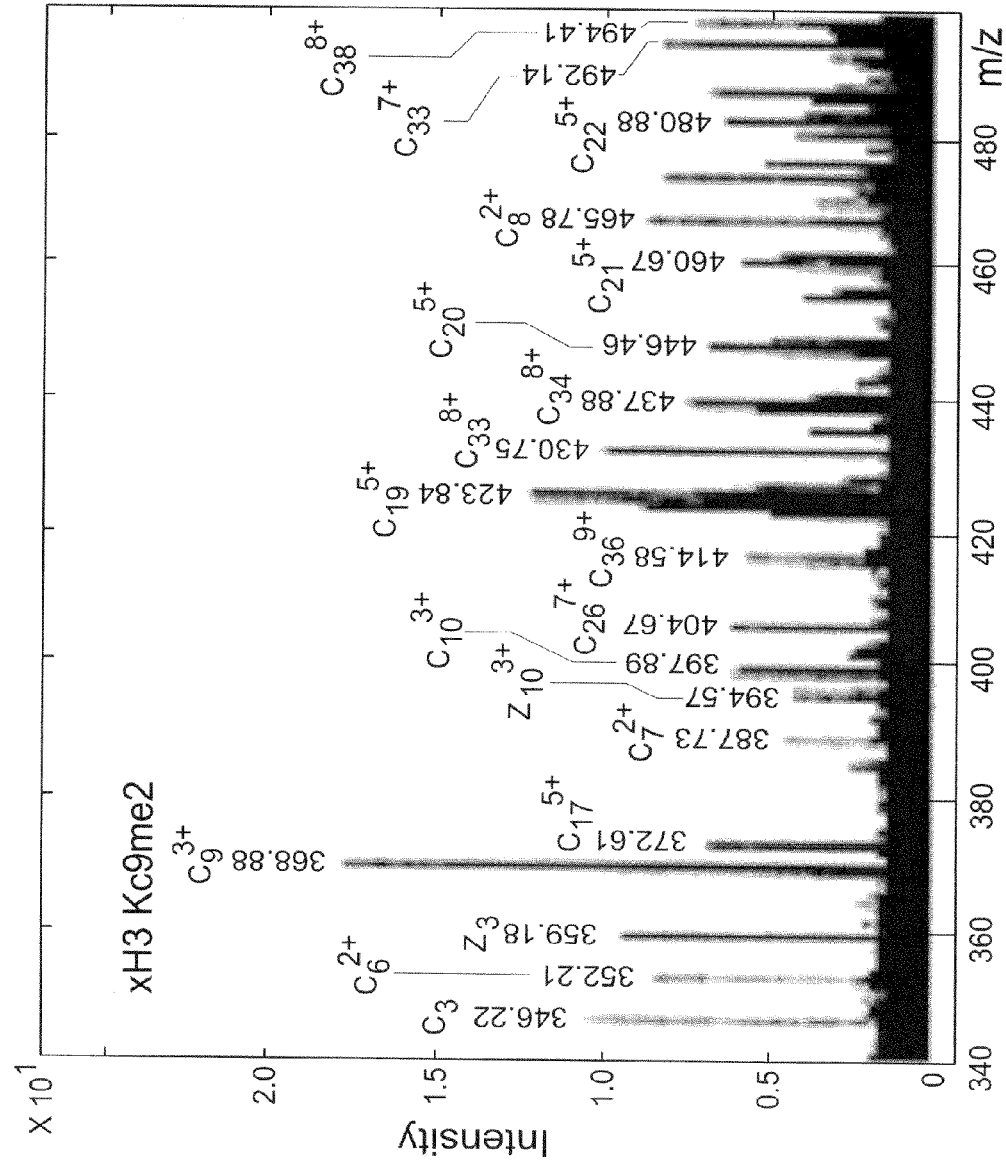
Fig. 2c (sheet 3)

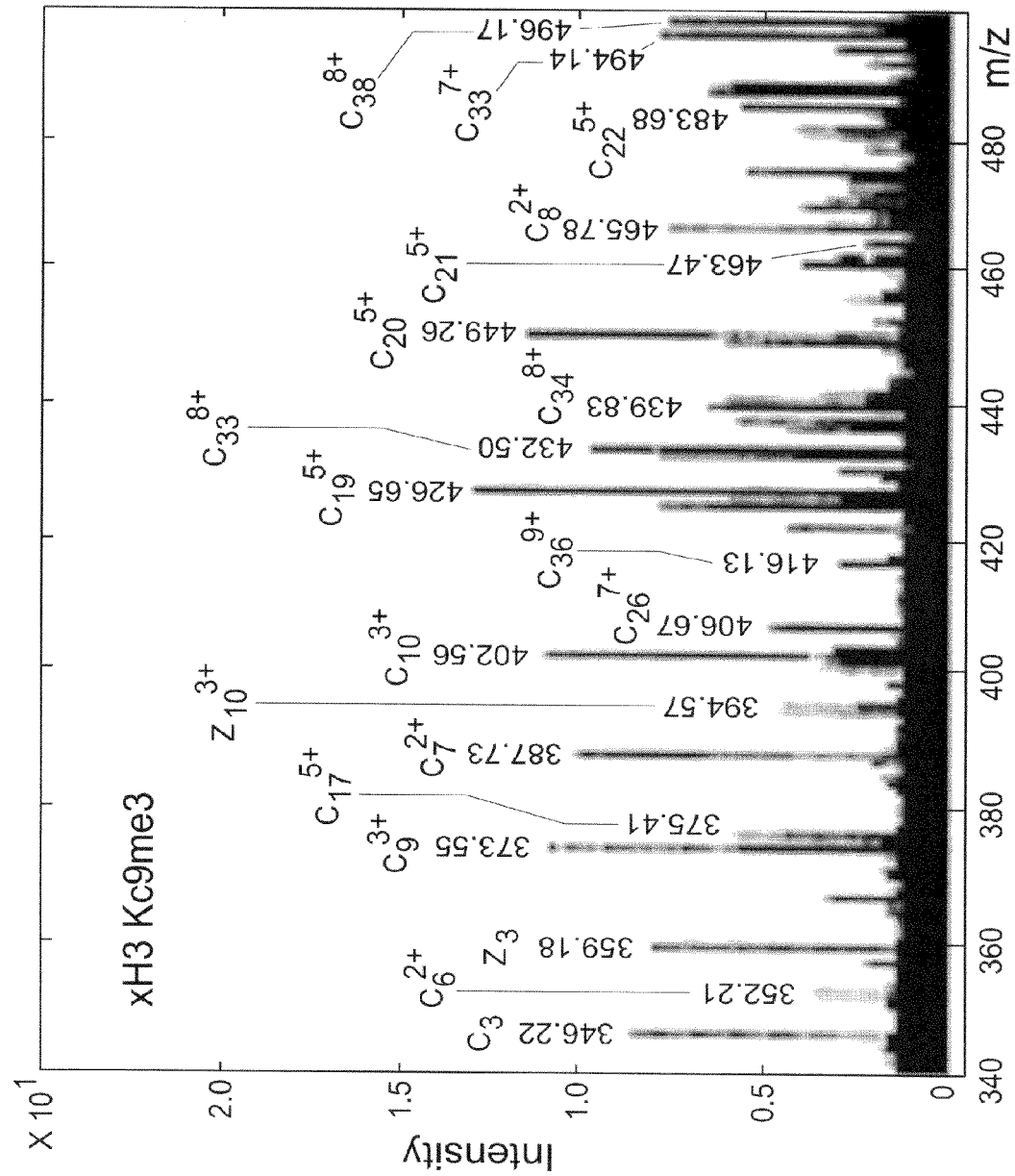
Fig. 2c (sheet 4)

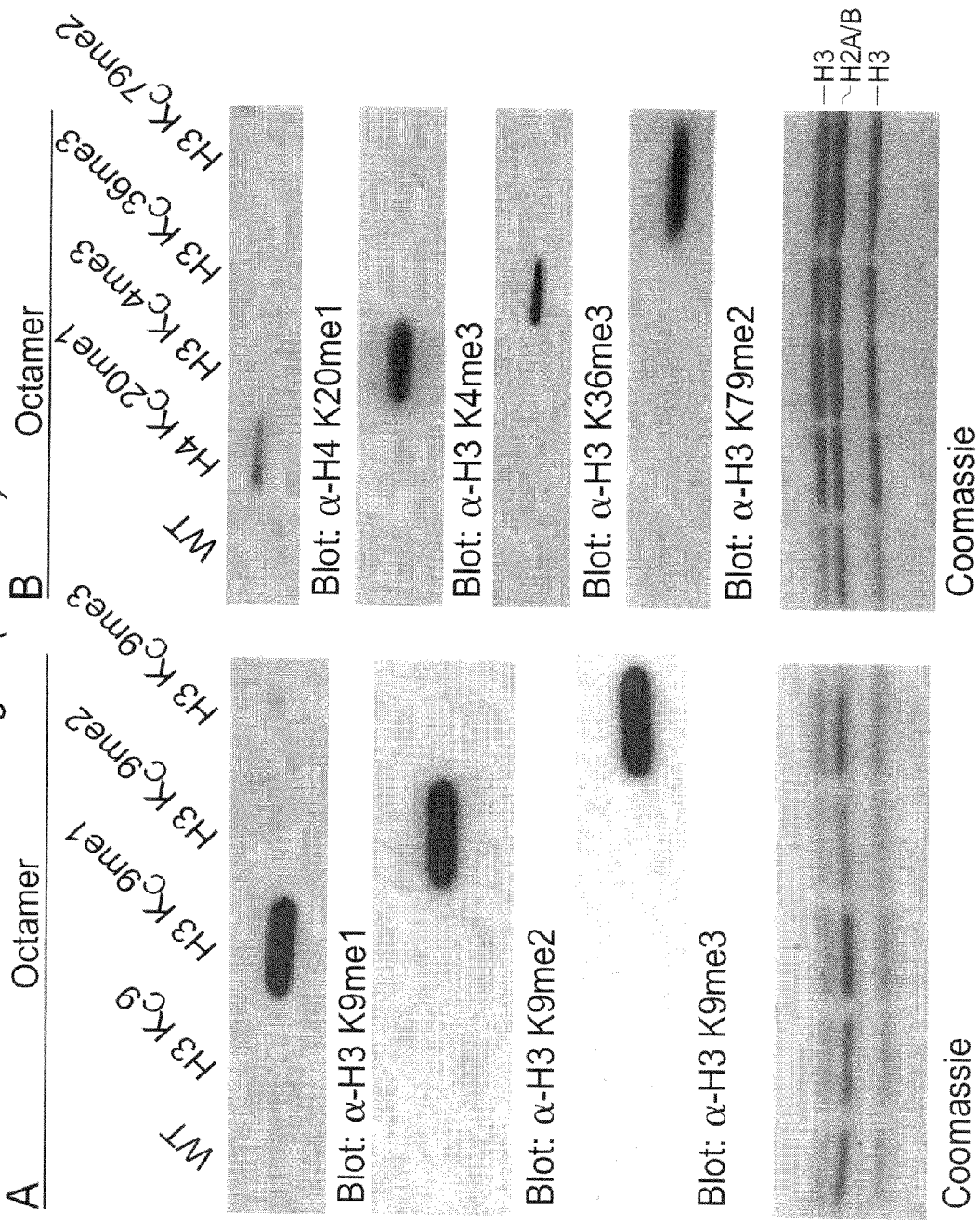
Fig. 3 (sheet 1)

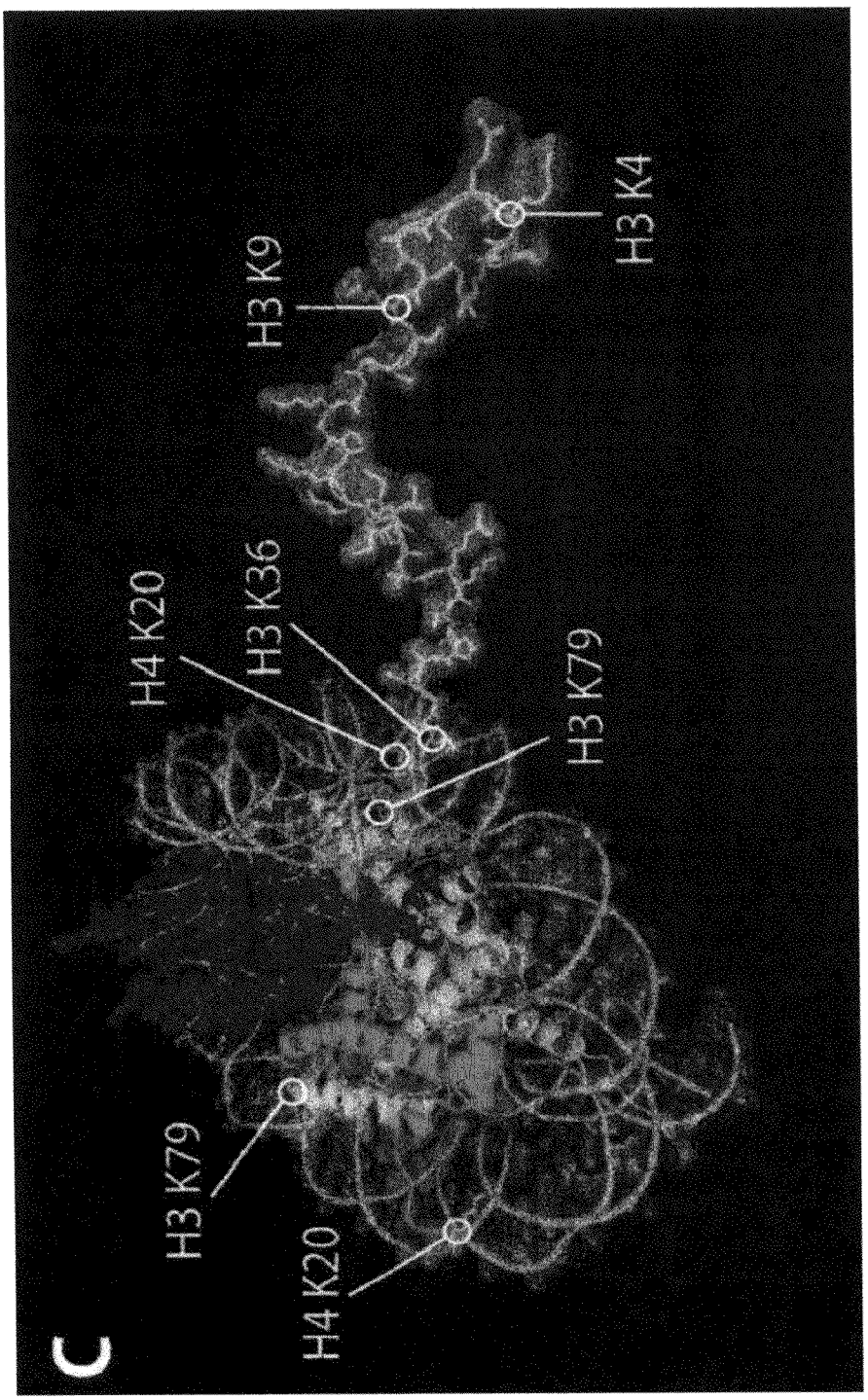
Fig. 3 (sheet 2)

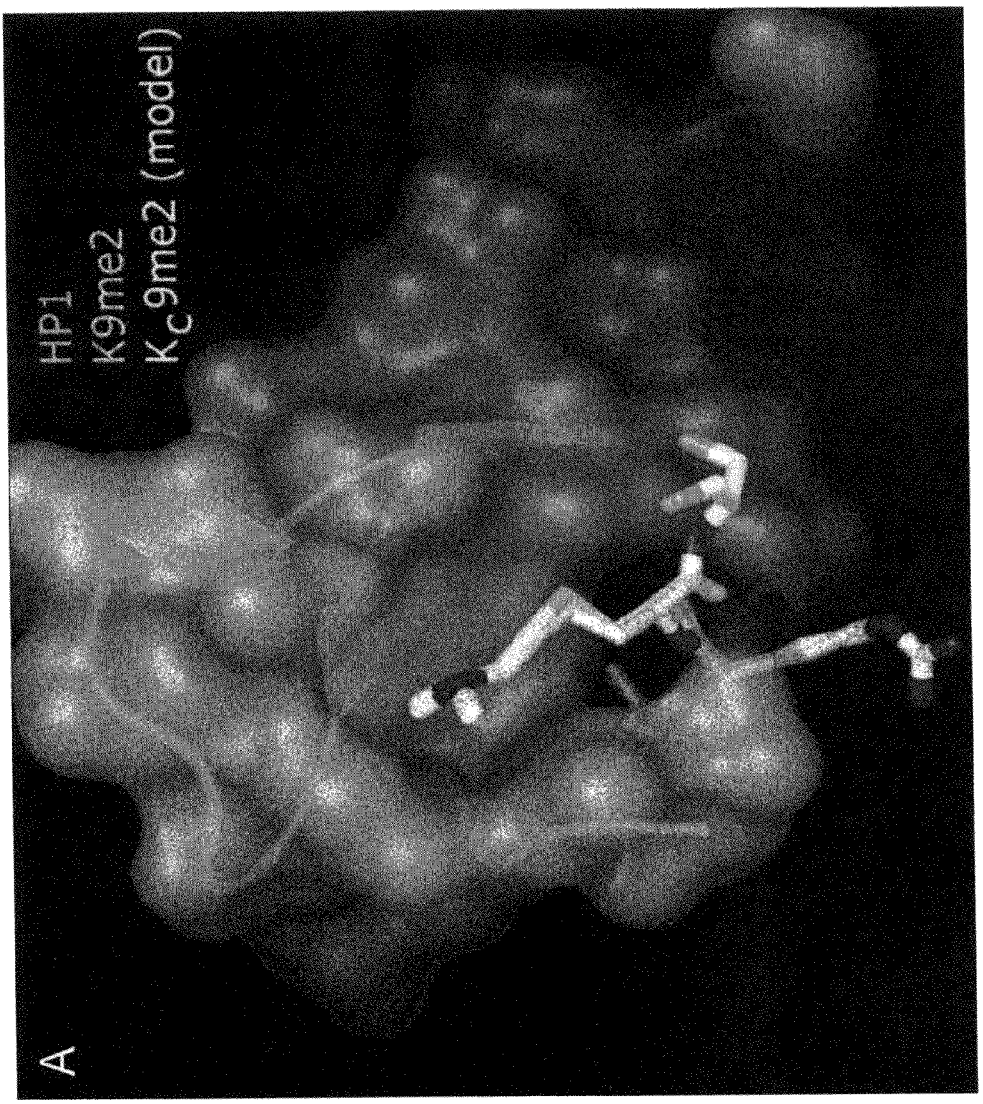
Fig. 4 (sheet 1)

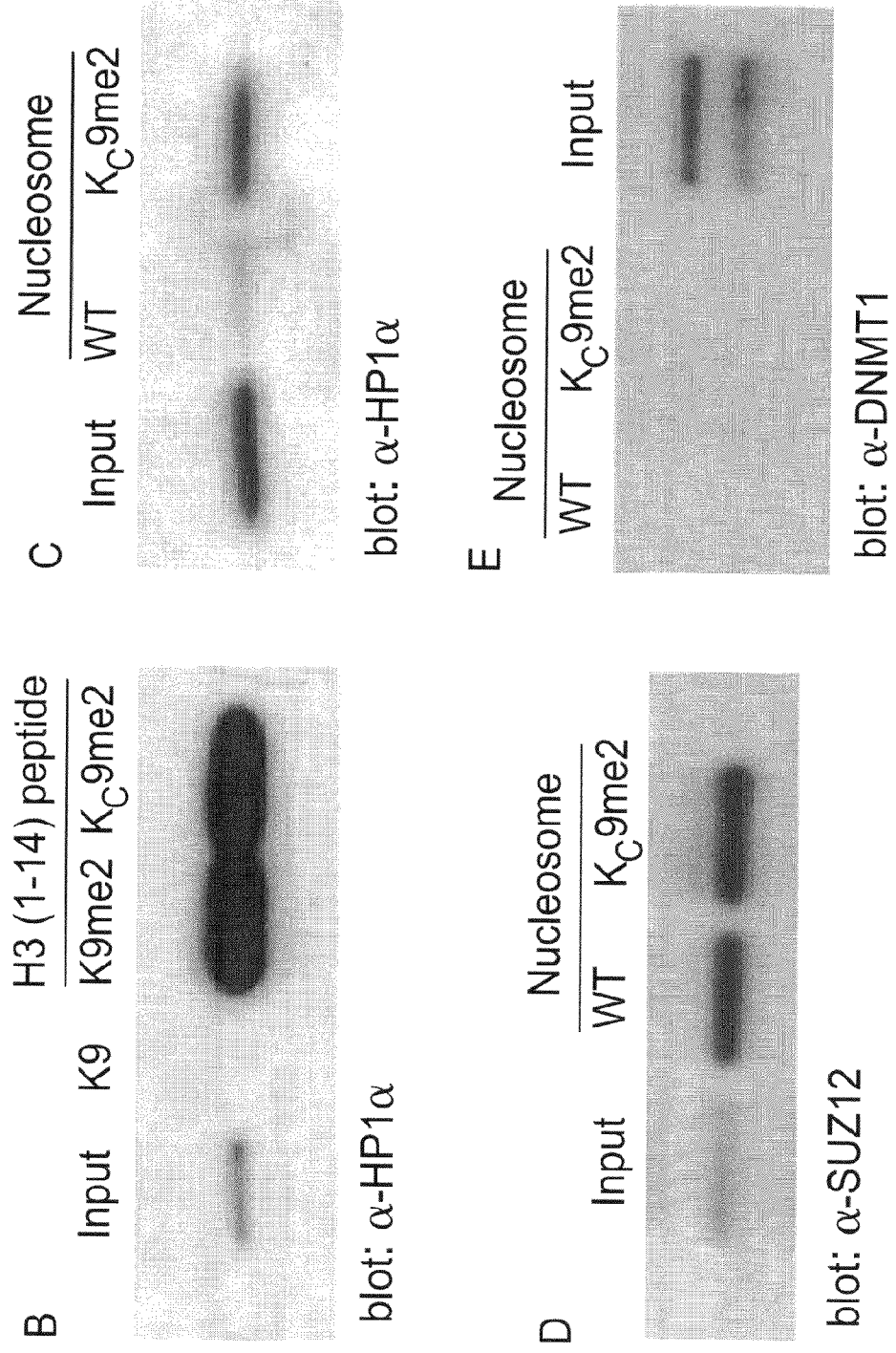
Fig. 4 (sheet 2)

Fig. 5 (sheet 1)
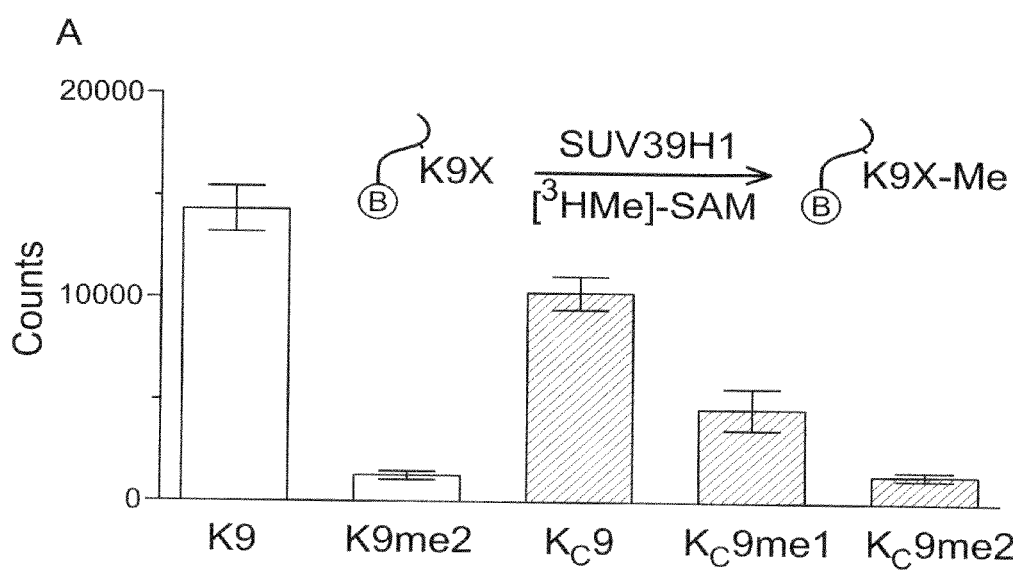
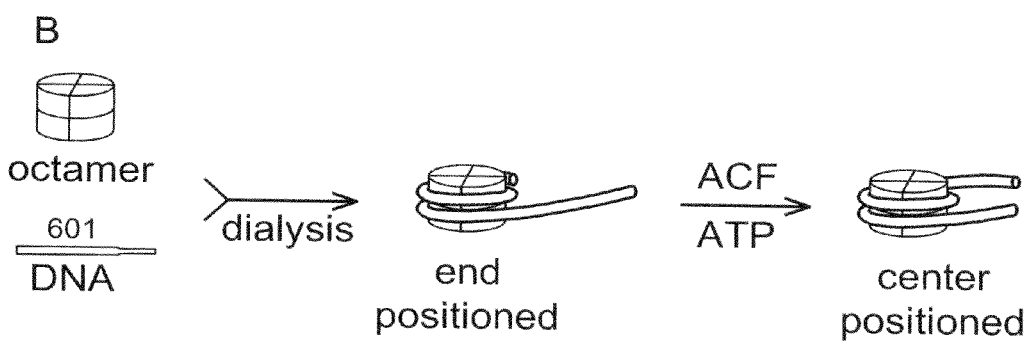

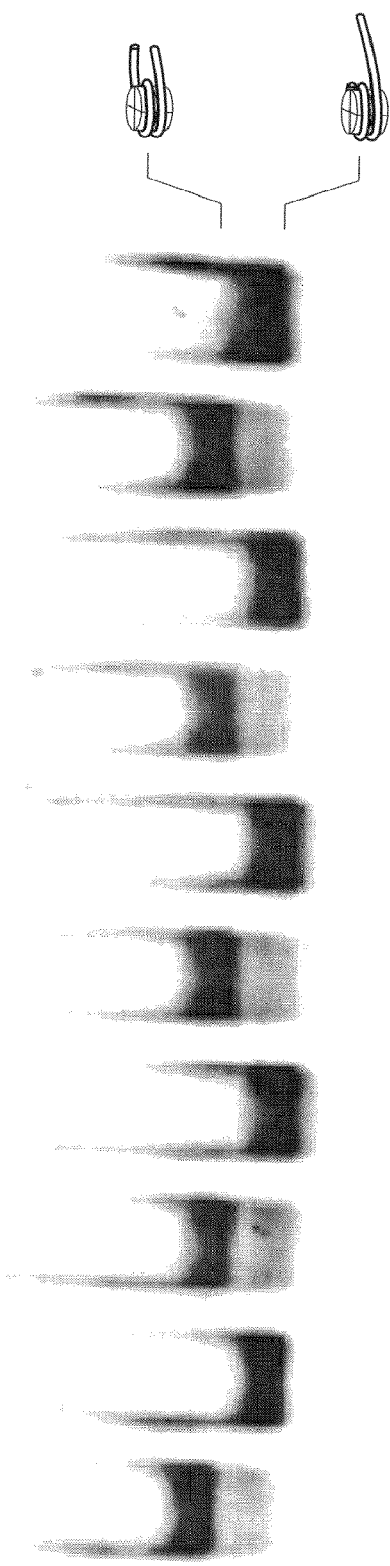

Fig. 5 (sheet 3)
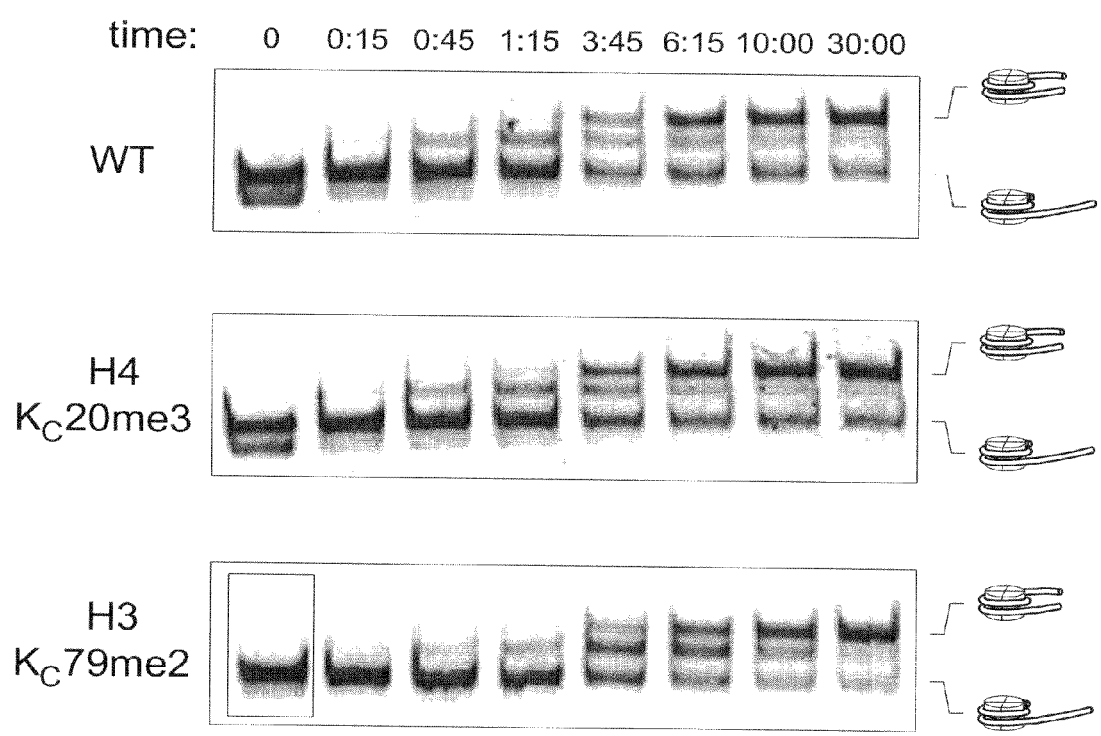

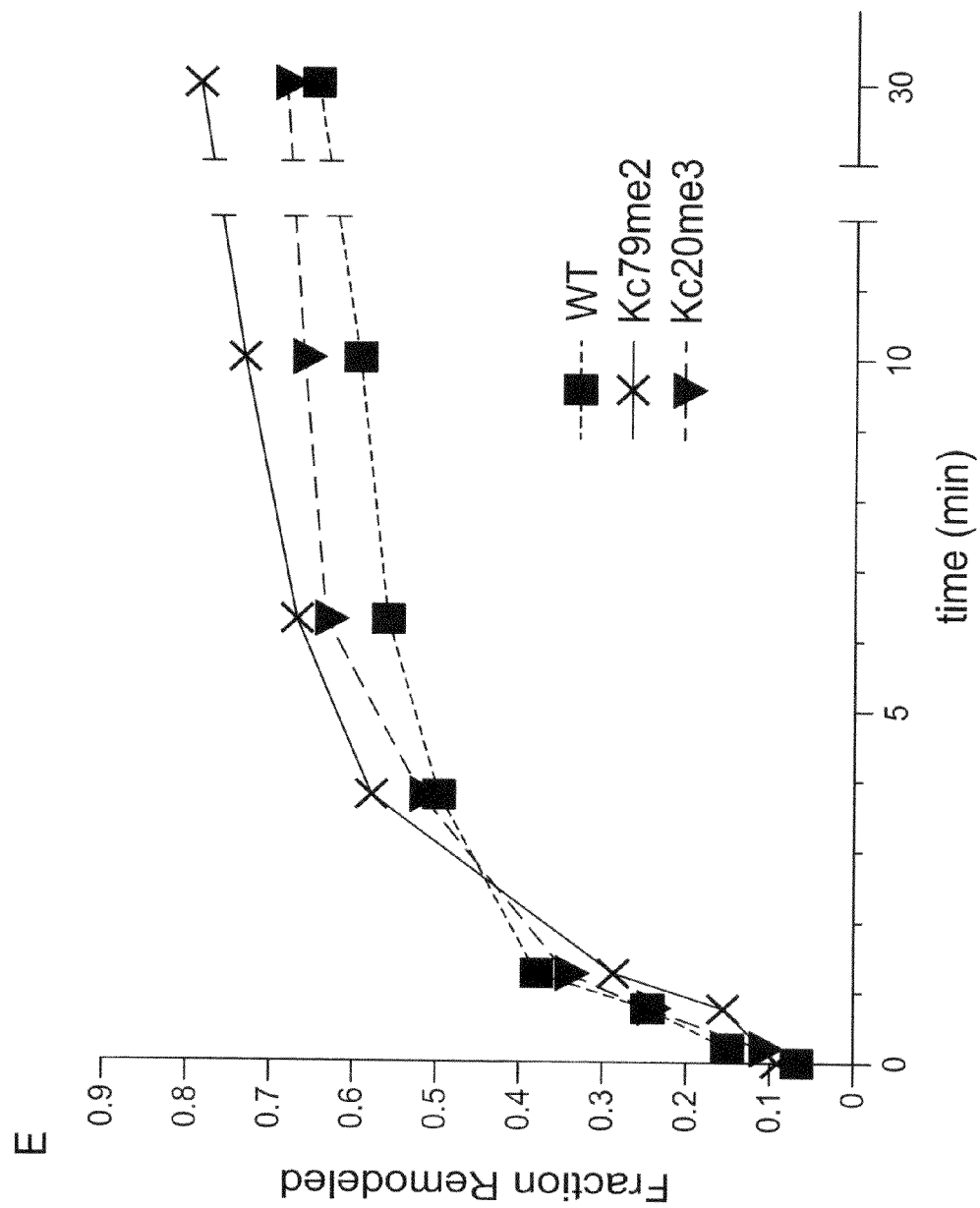
Fig. 5 (sheet 4)

Example ESI-oa TOF spectra used to optimize reaction conditions for installation of MLAs into full length histones Fig. 9
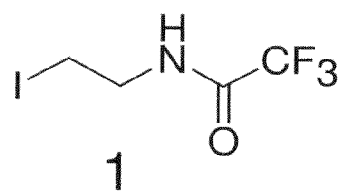
1
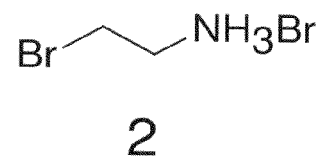
2
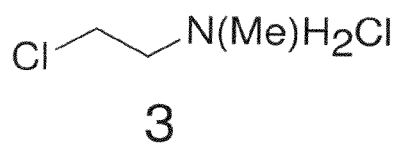
3
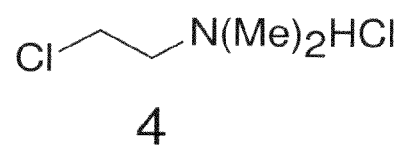
4
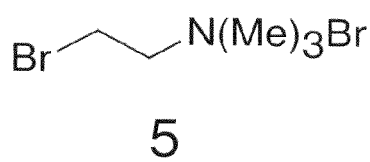
5
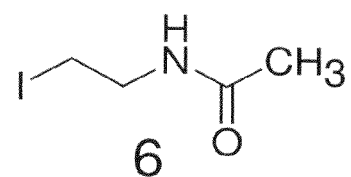
6

SITE-SPECIFIC INSTALLATION OF METHYL-LYSINE ANALOGUES INTO RECOMBINANT HISTONES

CROSS-REFERENCES TO RELATED APPLICATIONS

The present application claims priority to U.S. Ser. No. 60/876,680, filed Dec. 21, 2006.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

Biological signaling cascades frequently involve the covalent modification of proteins. Lysine is a frequent target of such post-translational modifications; in particular, the epsilon-amine of lysine can be substituted with one, two or three methyl groups and can be acetylated. While these modifications have been found in the context of many proteins, particularly noteworthy is the role of lysine post-translational modification in the context of histones, the proteins that serve as the foundation of chromatin. The basic unit of chromatin is the nucleosome, composed of 147 bp of DNA wrapped around an octamer of histones. Lysine methylation and acetylation have been demonstrated to play an important role in the regulation of chromatin structure and thereby are involved in the regulation of processes including transcription, DNA-repair and replication.

Studies in model organisms implicate histone lysine methylation as particularly important for defining the epigenetic status of a cell. The ε-amine of lysine is subject to mono-, di-, or trimethylation. Each methylation state may have a distinct regulatory impact through modulating the binding of different effector proteins (Martin, C. and Zhang, Y., *Nat Rev Mol Cell Biol*, 6:838-849(2005); Sims, R. J., 3rd et al., *Trends Genet*, 19:629-639 (2003)). Consistent with this notion, plant homeodomains (PHD) in the NURF remodeling complex and in the tumor suppressor ING2 bind with specificity for trimethylated over dimethylated Lys4 of histone H3 (Li, H. et al., *Nature*, 442:91-95 (2006); Pena, P. V. et al., *Nature*, 442:100-103 (2006); Shi, X. et al., *Nature*, 442:96-99 (2006); Wysocka, J. et al., *Nature*, 442:86-90 (2006)). The functional consequences of lysine methylation, in addition to being degree dependant, are also determined by the site of methylation (Lachner, M. et al., *J Cell Sci*, 116:2117-2124 (2003)). For example, while trimethylation at Lys4 is associated with euchromatin and transcriptional activation (Santos-Rosa, H. et al., *Nature*, 419:407-411 (2002)), trimethylation of H3 Lys9 is a well-established marker of heterochromatin and associated with transcriptional repression (Lee, D. Y. et al., *Endocr Rev*, 26:147-170 (2005); Rea, S. et al., *Nature*, 406:593-599 (2000)).

Recent years have seen the identification of numerous enzymes responsible for lysine methylation and demethylation, as well as down-stream effectors that bind to specific methyl lysine residues in histones (Grewal, S. I., and Moazed, D., *Science*, 301:798-802(2003); Martin, C. and Zhang, Y., *Nat Rev Mol Cell Biol*, 6:838-849(2005)). For instance, the Lys9-specific methyltransferase SUV39H1 (and its orthologues in other organisms) has been implicated in transcriptional silencing (Ivanova, A. V. et al., *Nat Genet*, 19:192-195 (1998); Rea, S. et al., *Nature*, 406:593-599 (2000)) and interacts genetically and biochemically with the heterochromatin associated protein HP1α (and its orthologues). Indeed, Lys9 methylation is recognized by the chromodomain of HP1α, which itself recruits SUV39H1 and is believed to oligomerize, causing a repressive chromatin structure by spreading along the chromatin (Grewal, S. I., and Moazed, D., *Science*, 301:798-802(2003)).

Methyl lysine residues in nucleosomal histones are hypothesized to mediate interactions with the macromolecular complexes that regulate transcription, replication, and DNA-repair. Investigating how lysine modifications influence the activity of these factors would be facilitated by a biochemical system that allows testing of specific methylation patterns on any histone. In particular, nucleosomes reconstituted from homogeneous preparations of recombinant histones, ideally with every possible methylation state at each site of interest, would allow systematic examination of the events downstream of lysine methylation.

Current methods to introduce methylation into recombinant histones include biosynthetic approaches or semi-synthesis. The use of enzymes to methylate lysine residues is limited by the availability of specific methyltransferases. Even in cases where an appropriate methyltransferase is available, these reactions are difficult to drive to completion and can lead to uncontrolled degrees of methylation or heterogeneity with respect to site-specificity.

Semi-synthetic methods to construct modified histones using native chemical ligation have been reported (He, S. et al., *Proc Natl Acad Sci USA*, 100: 12033-12038 (2003); Shogren-Knaak, M. A. et al., *J Biol Chem*, 278:15744-15748 (2003); Shogren-Knaak, M. A. and Peterson, C. L., *Methods Enzymol*, 375:62-76 (2004)). This approach was instrumental in demonstrating a role for H4 Lys 16 acetylation in antagonizing chromatin compaction (Shogren-Knaak, M. et al., *Science*, 311:844-847 (2006)), underscoring the utility of homogeneously modified histones for investigating the impact of lysine modifications on chromatin function. Nonetheless, the semisynthesis of modified histones is currently limited to modifications at only N-terminal residues (residues 1-30) and requires the synthesis of large quantities of modified peptide thioesters.

Thus, there is a need in the art for improved reagents and methods for the generation of histone proteins with site specific post-translations modifications, particularly methylation or acetylation. One need in the art is an efficient means to reconstitute nucleosomes with site-specific mono, di- and trimethylation at positions throughout the entire sequence of each histone.

BRIEF SUMMARY OF THE INVENTION

Histone lysine residues can be mono-, di-, or trimethylated. These post-translational modifications regulate the affinity of effector proteins and may also impact chromatin structure independent of their role as adaptors. Another important modification of histones is acetylation. In order to study histone lysine methylation and acteylation, particularly in the context of chromatin, we have developed a chemical approach to install analogues of methyl or acetyl-lysine into recombinant proteins. This approach allows for the rapid generation of large quantities of histones in which the site and degree of methylation or acetylation can be specified. We demonstrate that these methyl or acetyl-lysine analogues are functionally similar to their natural counterparts.

In one embodiment, this invention provides a method of introducing a site specific mono-, di, or tri-methylated lysine residue analogue into a histone protein comprising the steps of: (a) mutating selected cysteine residues in the native sequence of the histone protein to an amino acid residue that does not affect the function of the histone protein, (b) mutating at least one lysine residue in the amino acid sequence of the histone protein to a cysteine residue to generate a cysteine containing protein, and (c) contacting the cysteine containing protein with a compound of the structure: R—CH$_2$CH$_2$—NH(Me)$_x$, where R is a leaving group and x is 0, 1, 2, or 3, thereby introducing a site specific mono-, di, or tri-methylated lysine residue analogue into a histone protein. In one aspect of this embodiment, the amino acid residue that does not affect the function of the histone protein can be alanine. In another aspect of this embodiment, R is a halide, including Cl, Br, or I. In other aspects, R can be mesylate or tosylate. In further aspects of this embodiment, the histone protein can be histone H3 or H4, and the specific lysine residues altered to cysteine include K4, K9, K14, K27, K36, or K79 of histone H3, and K5, K8, K12, K16, or K20 of histone H4. In further aspects of this embodiment, the cysteine containing protein is treated with a reducing agent prior to step (c) using a reducing agent such as DTT.

In another embodiment, the invention provides an isolated histone protein comprising a lysine to cysteine substitution, wherein said cysteine substitution comprises the side chain structure —S—CH$_2$CH$_2$—NH(Me)$_x$, where x is 1, 2, or 3. In an aspect of this embodiment, the histone protein can be histone H3 or H4, and the specific lysine residues altered to cysteine include K4, K9, K14, K27, K36, or K79 of histone H3, and K5, K8, K12, K16, or K20 of histone H4.

In a further embodiment of this invention, an isolated histone protein comprising site specific mono-, di, or tri-methylated lysine residue analogues derived by a process comprising the steps of: (a) mutating selected cysteine residues in the native sequence of the histone protein to alanine, (b) mutating at least one lysine residue in the sequence of the protein to a cysteine residue to generate a cysteine containing protein, and (c) contacting the cysteine containing protein with a compound of the structure: R—CH$_2$CH$_2$—NH(Me)$_x$, where R is a leaving group and x is 0, 1, 2, or 3 is provided. In an aspect of this embodiment, R is a halide, including Cl, Br, and I. In other aspects, R can be mesylate or tosylate. In further aspects of this embodiment, the histone protein can be histone H3 or H4, and the specific lysine residues altered to cysteine include K4, K9, K14, K27, K36, or K79 of histone H3, and K5, K8, K12, K16, or K20 of histone H4.

In another embodiment, this invention provides a method for assaying the effect of methylation of at least one lysine residue on a histone protein on the histone protein's activity comprising the steps of: (a) mutating selected cysteine residues in the native sequence of the histone protein to alanine, (b) mutating at least one lysine residue in the sequence of the histone protein to a cysteine residue to generate a cysteine containing histone protein; (c) contacting the cysteine containing histone protein with a compound of the structure: R—CH$_2$CH$_2$—NH(Me)$_x$, wherein R is a leaving group and x is 0, 1, 2, or 3 to generate a methylated protein, and (d) comparing the activity of the methylated histone protein with the histone protein without the mutation or with a protein derived after step (c) in which x is 0, thereby assaying the effect of methylation of at least one lysine residue on the histone protein's activity. In some aspects of this embodiment, the assay comprises measuring octomer reconstitution or nucleosome remodeling.

In yet a further embodiment, this invention provides a method of introducing a site specific acetylated lysine residue analogue into a histone protein comprising the steps of: (a) mutating selected cysteine residues in the native sequence of the histone protein to an amino acid residue that does not affect the function of the histone protein, (b) mutating at least one lysine residue in the amino acid sequence of the histone protein to a cysteine residue to generate a cysteine containing protein, and (c) contacting the cysteine containing protein with a compound of the structure: R—CH$_2$CH$_2$—NH(Ac)$_x$, where R is a leaving group and x is 0, 1, or 2, thereby introducing a site specific acetylated lysine residue analogue into a histone protein.

An additional embodiment of this invention provides an isolated histone protein comprising site specific acetylated lysine residue analogues derived by a process comprising the steps of: (a) mutating selected cysteine residues in the native sequence of the histone protein to alanine, (b) mutating at least one lysine residue in the sequence of the protein to a cysteine residue to generate a cysteine containing protein, and (c) contacting the cysteine containing protein with a compound of the structure: R—CH$_2$CH$_2$—NH(Ac)$_x$, where R is a leaving group and x is 0, 1, or 2.

A further embodiment of this invention provides a method for assaying the effect of acetylation of at least one lysine residue on a histone protein on the histone protein's activity comprising the steps of: (a) mutating selected cysteine residues in the native sequence of the histone protein to alanine, (b) mutating at least one lysine residue in the sequence of the histone protein to a cysteine residue to generate a cysteine containing histone protein, (c) contacting the cysteine containing histone protein with a compound of the structure: R—CH$_2$CH$_2$—NH(Ac)$_x$, where R is a leaving group and x is 0, 1, or 2 to generate an acetylated protein, and (d) comparing the activity of the acetylated histone protein with the histone protein without the mutation or with a protein derived after step (c) in which x is 0, thereby assaying the effect of acetylation of at least one lysine residue on the histone protein's activity.

BRIEF DESCRIPTION OF THE DRAWINGS

FIG. 1. The installation of methyl lysine analogues into recombinant proteins by alkylating cysteine residues.

Figure 2A:
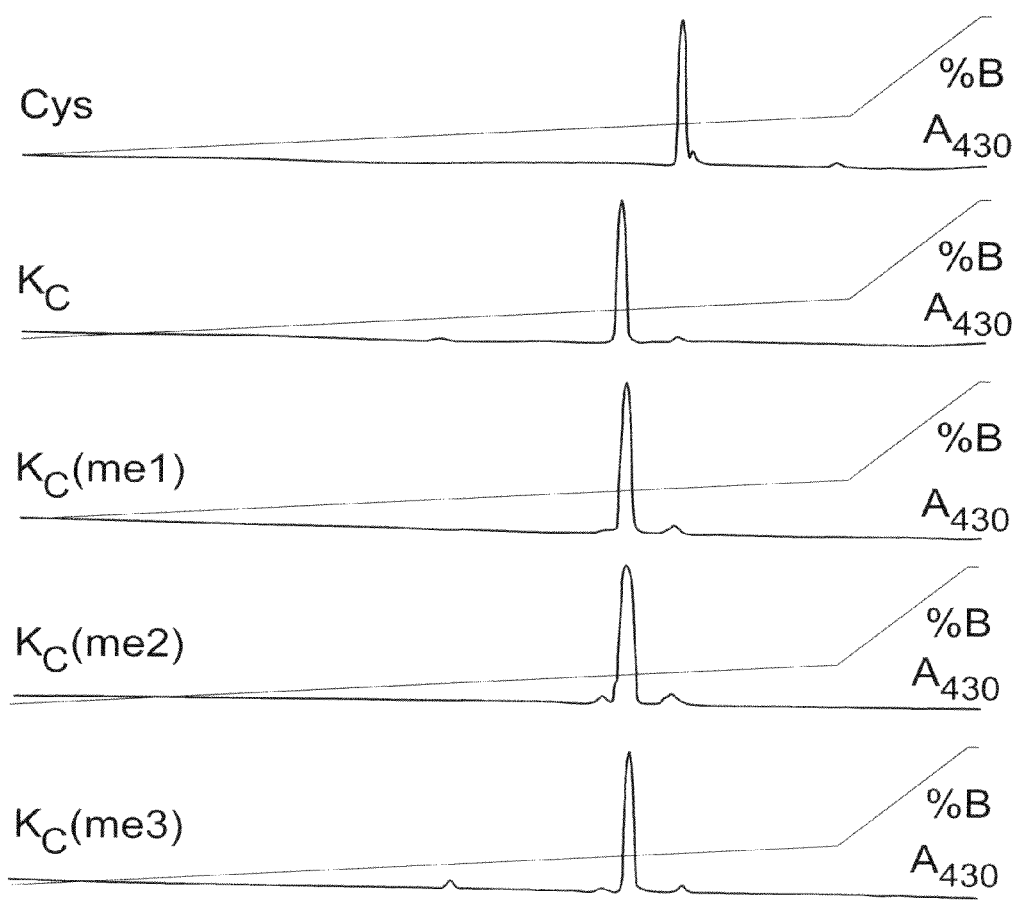

(A) The MLA strategy is an extension of the traditional aminoethylation reaction in which a cysteine is alkylated with an electrophilic ethylamine producing aminoethylcysteine, an analogue of lysine.

(B) Cysteine residues can be converted into analogues of mono-, di- and trimethylated lysine by treatment with alkylating agents 1-3, respectively.

(C) Incubating 2 under basic conditions leads to aziridinium formation. The resulting aziridinium can react with a cysteine residue leading to the desired dimethyl lysine analogue.

FIG. 2. Cysteine residues can be efficiently converted into MLAs in the context of peptides and full-length proteins.

(A) A cysteine-containing peptide (Fluorescein-KACR-OH) is converted to the desired lysine analogue under optimized reaction conditions (see Experimental Procedures) as observed by reverse phase HPLC analysis of the crude reaction products. The traces are for the starting peptide (Cys); the unmethylated lysine analogue, K$_c$; the monomethylated lysine analogue, K$_c$(me1); the dimethylated lysine analogue, K$_c$(me2); and the trimethylated lysine analogue, K$_c$(me3).

(B) Mass spectra (ESI-oaTOF) demonstrate that MLAs can be cleanly installed at position 9 of full-length histone H3 protein. Starting with a K9C mutation (top left), this histone was treated under conditions to install analogues of monomethyl Lys9 H3 (top right), dimethyl Lys9 H3 (bottom left), or trimethyl Lys9 H3 (bottom right). The asterisk indicates a peak at +42 daltons corresponding to an artifact and is present in both the starting material and the methylated histone products.

(C) Representative ECD spectra of full-length histones acquired from a FT-ICR mass spectrometer are consistent with the installation of desired analogues at histone H3 residue 9.

FIG. 3. MLAs can be incorporated into histone octamers and are specifically recognized by antibodies raised against the corresponding natural modifications.

(A) Western blot analysis of octamers assembled with MLAs at various tail and core positions.

(B) The positions of modifications from (A) mapped onto a model of a nucleosome (based on Luger, K. et al., *J Mol Biol,* 272:301-311 (1997)).

FIG. 4. Methyl Lys9 analogues behave similarly to their natural counterparts in binding assays.

(A) Based on the crystal structure of HP1 (green) bound to a K9me2 peptide (grey backbone, PDB:1KNA, from (Jacobs, S. A. and Khorasanizadeh, S., *Science,* 295:2080-2083 (2002)), a model of a $K_c$9me2 peptide (yellow backbone shown as overlay) bound to HP1 was constructed and minimized using MOLOC.

(B) Analysis of HP1α from 293 nuclear extracts binding to immobilized H3 tail peptides. Peptides (100 μg) with either unmodified lysine at position 9 (K9), with natural dimethylation at Lys9 (K9me2) or containing a dimethyl lysine analogue, $K_c$9me2, were used as affinity reagents and bound HP1α was monitored by western blot. In (B-E), input represent 5% of the starting nuclear extract.

(C) HP1α from nuclear extracts is specifically enriched upon binding to immobilized nucleosomes (100 pmol) assembled with H3 $K_c$9me2 relative to unmodified nucleosomes (WT).

(D) SUZ12 is enriched when using both $K_c$9me2 modified and unmodified (WT) nucleosomes as affinity reagents.

(E) DNMT1 does not pull down using either $K_c$9me2 modified or unmodified (WT) nucleosomes as affinity reagents.

FIG. 5. Analysis of MI-As as substrates in enzymatic assays.

(A) The Lys9 methyltransferase activity SUV39H1 was examined using [$^3$H-Me]-SAM and biotinylated H3 tail peptides (residues 1-14) containing either unmodified lysine at position 9 (K), dimethyl lysine (K9me2), aminoethylcysteine ($K_c$9), the monomethyl lysine analogue ($K_c$9me1) or the dimethyl lysine analogue ($K_c$9me2). Data are shown as white bars for peptides with natural lysine residues and as grey bars for lysine analogues.

(B) Schematic depicting the assembly and hACF-mediated remodeling of positioned mononucleosomes.

(C) Similar levels of hACF-mediated ATP-dependent remodeling activity are observed using nucleosomes with or without MLAs. Upon native gel electrophoresis, the migration of centrally positioned nucleomsomes is retarded relative to the migration of end positioned nucleosomes.

(D) The maximal rate of ACF-mediated nucleosome remodeling is not affected by $K_c$20me3 or $K_c$79me2 as demonstrated in a remodeling assay observed at several different time points.

(E) Graphical analysis of the results form (D) demonstrating similar rates of remodeling of WT and modified nucleosomes.

Figure 6:
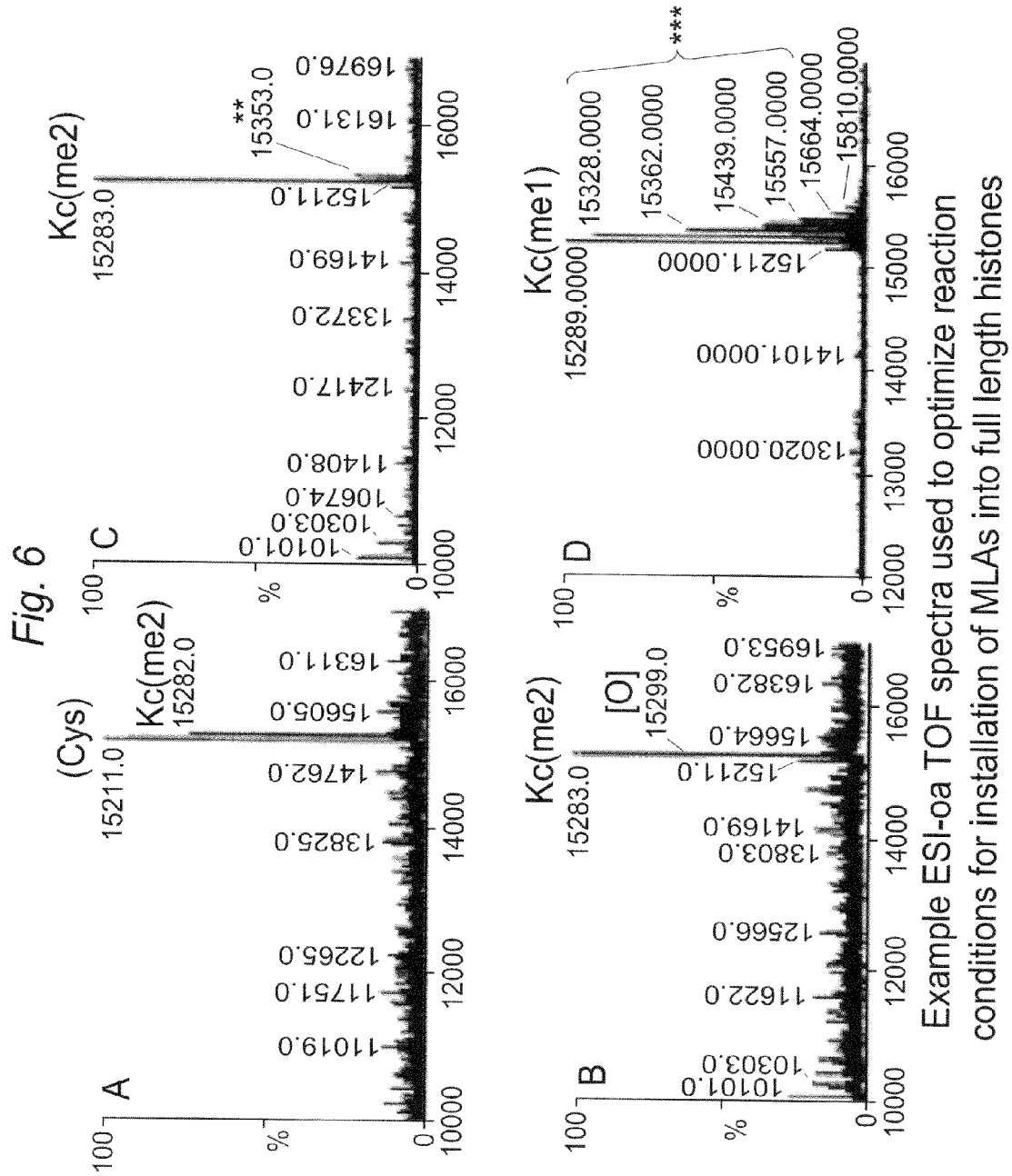

FIG. 6. Example of ESI-oaTOF spectra used to optimize reaction conditions for installation of MLAs into full length histones.

Figure 7:
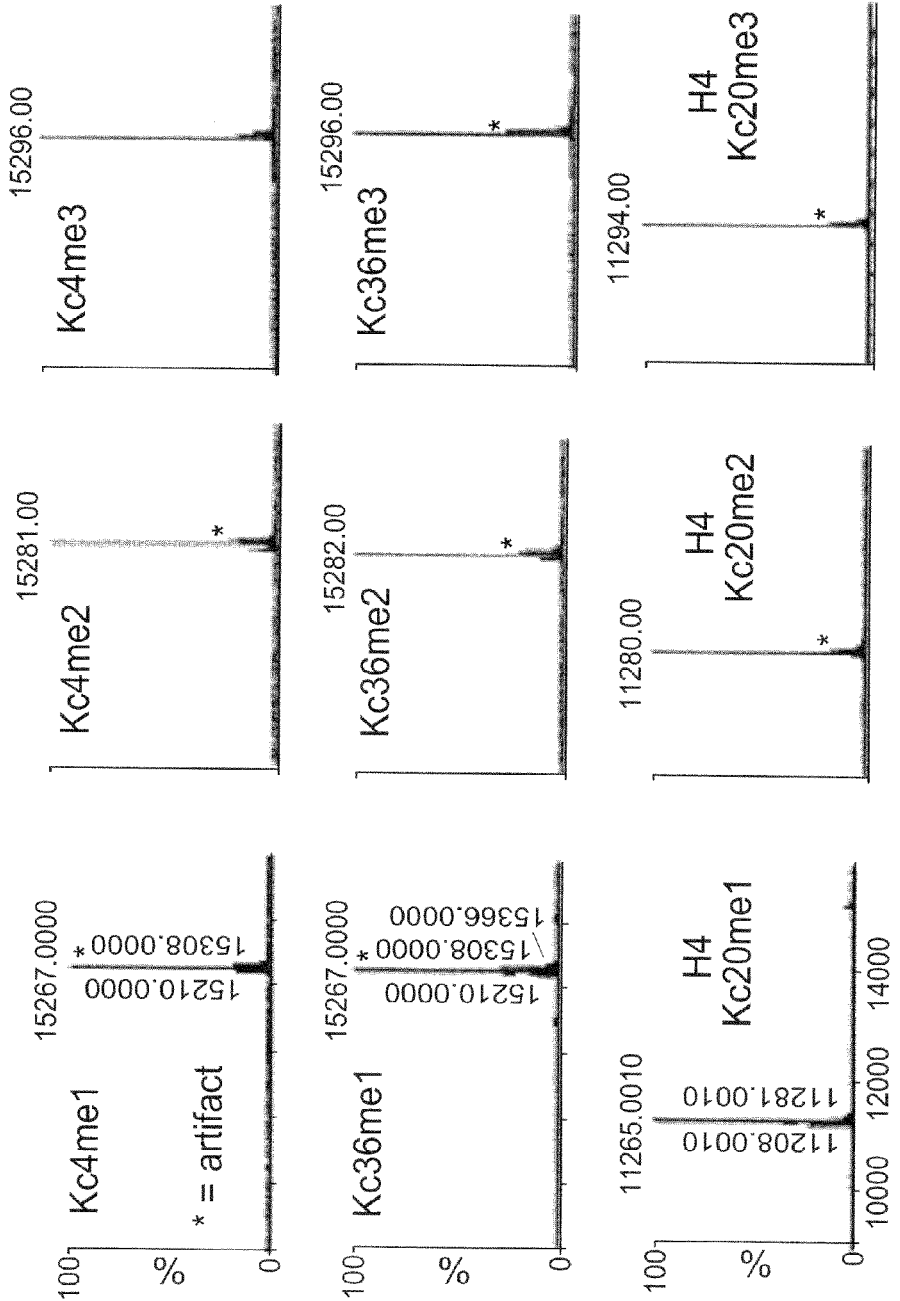

FIG. 7. Mass spectra (ESI-oaTOF) demonstrating the clean synthesis of mono-, di-, and trimethyl lysine analogues of histone H3 Lys4 and Lys36 and histone H4 Lys20 methylation. The asterisk indicates a peak at +42±1 dalton corresponding to an artifact.

Figure 8:
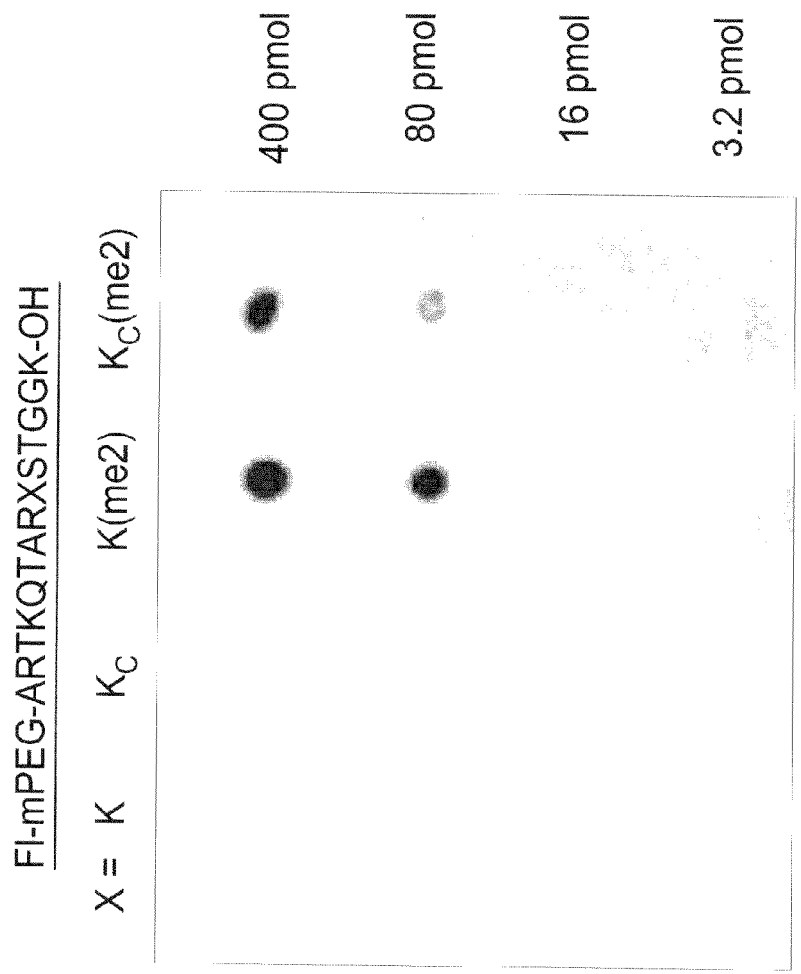

FIG. 8. Dot blot comparison of anti-histone H3 dimethyl-Lys9 antibody recognition of K9-modified peptides containing either K, lysine; $K_c$, aminoethylcysteine; K(me2), dimethyl-lysine; or $K_c$ (me2), dimethyl-aminoethylcysteine. Serial dilutions of the peptide (as indicated) were spotted on a PVDF membrane, allowed to dry overnight and probed essentially as described in Perez-Burgos, L. et al., *Methods Enzymol.,* 376:234-254 (2004).

FIG. 9. The structures of representative compounds that can be used to generate methyl and acetyl lysine analogues of histone proteins.

Figure 10:
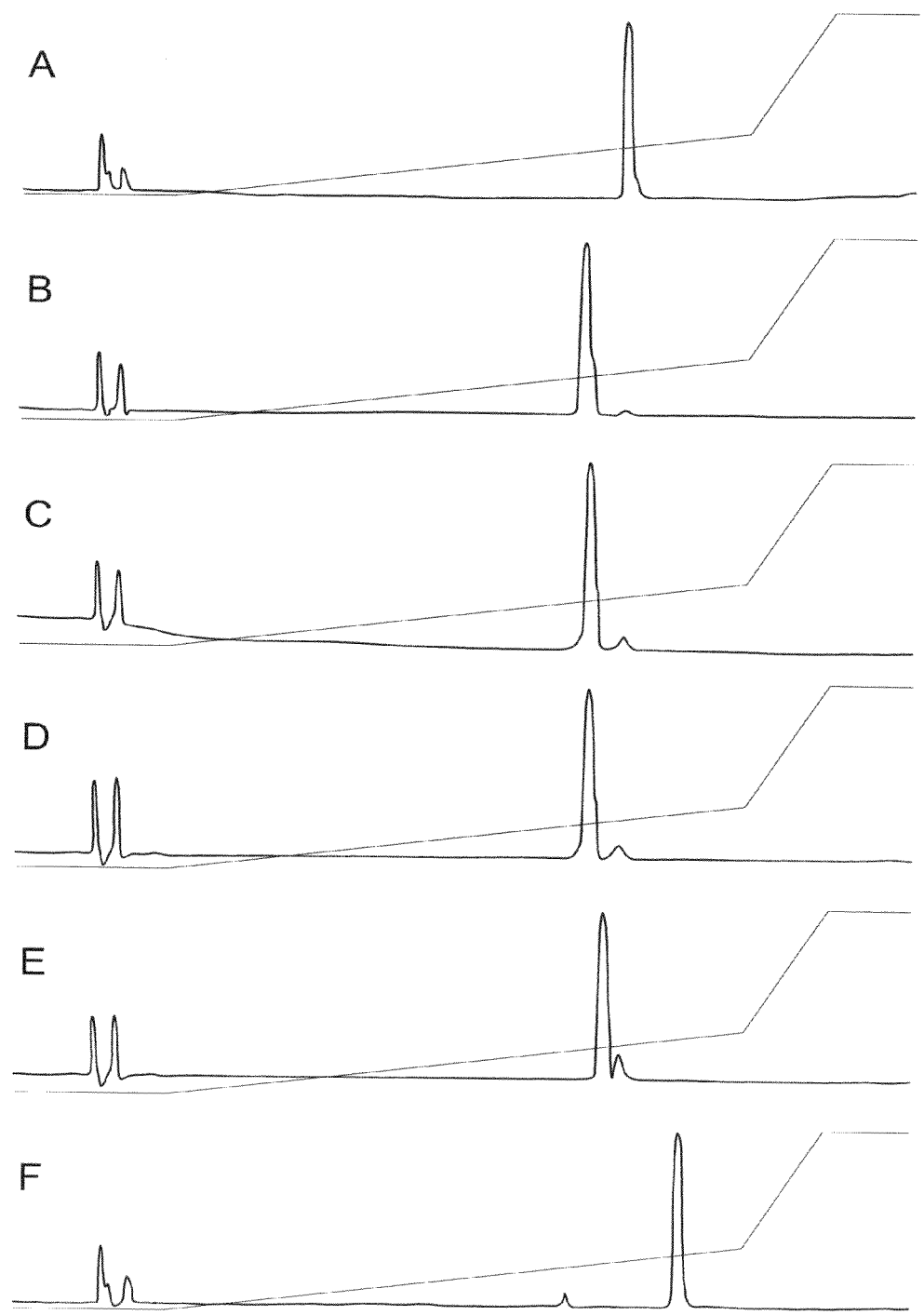

FIG. 10. HPLC chromatograms ($A_{430}$) of crude reaction products from the treatment of Fluoreceine-miniPEG-GACR-OH with alkylating agents 2-6. The cysteine of the starting material (A) was converted into (B) aminoethylcysteine, (C) methyl-aminoethylcysteine, (D) dimethyl-aminoethylcysteine, (E) trimethyl-aminoethylcysteine and (F) acetyl-aminoethylcysteine. The identities of the product peptides were confirmed by MALDI-TOF MS.

Figure 11:
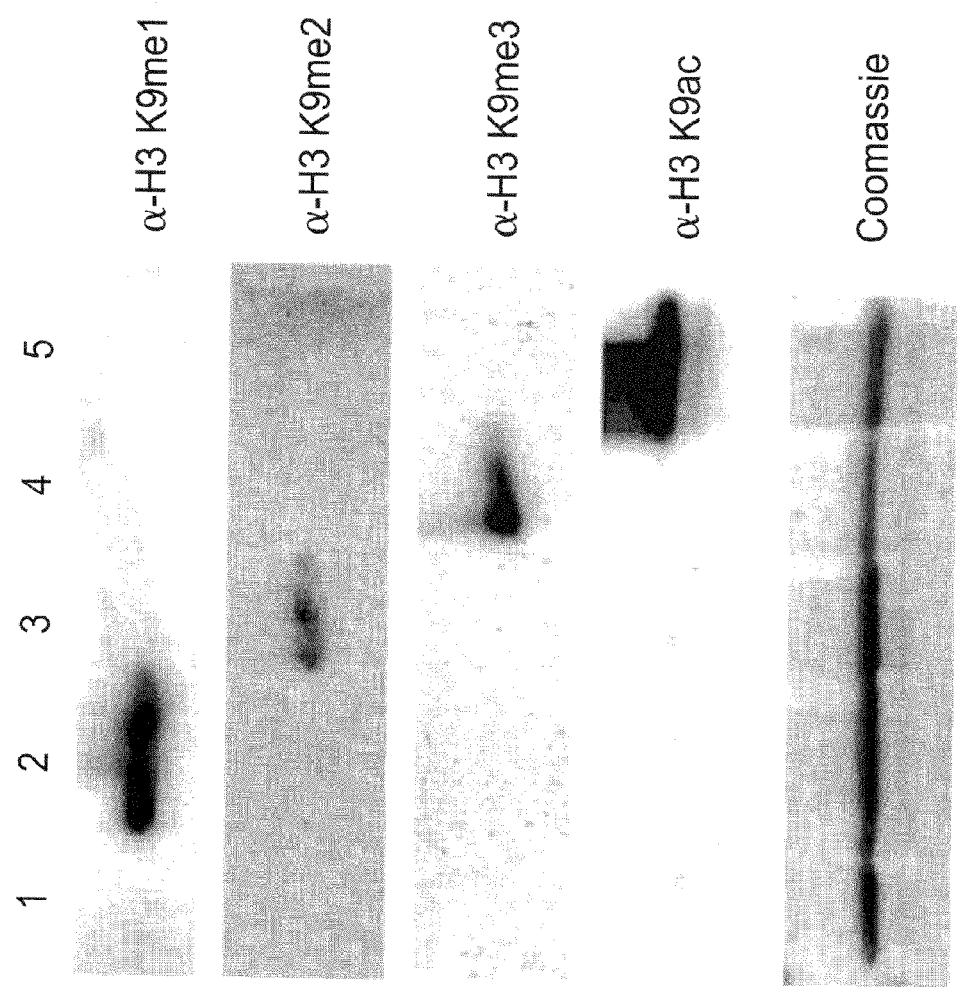

FIG. 11. FIG. 11 shows that full length histone H3 K9C C110A was installed with analogues of lysine (lane 1), methyl-lysine (lane 2), dimethyl lysine (lane 3), trimethyl-lysine (lane 4) or acetyl-lysine (lane 5) at position 9 of the histone tail. These proteins were probed by western blot using the indicated antibodies.

Figure 12:
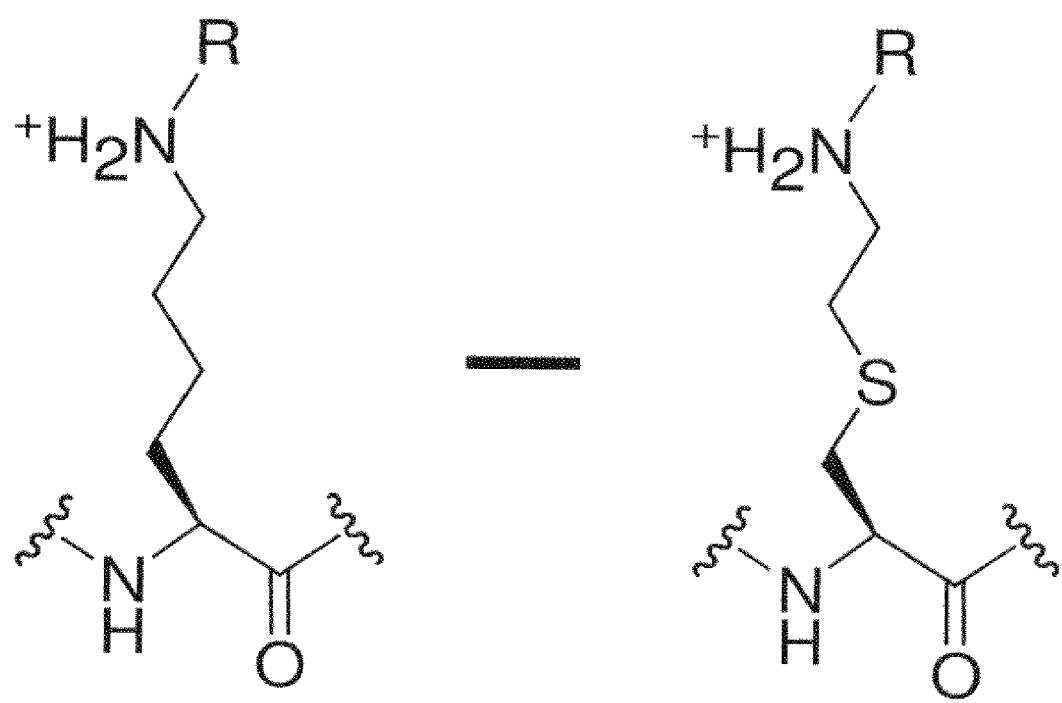

FIG. 12. FIG. 12 shows that post-translationally modified lysine is approximately isosteric to an N-substituted aminoethylcysteine.

DETAILED DESCRIPTION OF THE INVENTION

I. Introduction

Many of the pre-existing methods to effect quantitative methylation of lysine residues on histone proteins suffer from disadvantages which limit their usefulness. For instance, methods to chemically methylate lysine residues, such as reductive alkylation (Means, G. E. and Feeney, R. E., *Biochemistry,* 7:2192-2201 (1968)), are not amenable to controlling which of the numerous histone lysine residues are modified. Thus, the direct site-specific methylation of lysine residues on histones has remained a challenging goal using the pre-existing technology. As an alternative to such existing methods, we have exploited the latent reactivity of natural amino acid side-chains to chemically generate histones with site and degree-specific methylation. We have identified cysteine as an attractive target for chemical elaboration due to its distinctive reactivity as a nucleophile. Specifically, we have discovered that alkylation of a cysteine residue, installed at the desired site of modification, via an aminoethylation reaction, can be used to create aminoethylcysteine, an analogue of lysine (see FIG. 1A, and Kenyon, G. L. and Bruice, T. W., *Methods Enzymol,* 47:407-430 (1977) for a general discussion of this reaction). In the present invention, we have used an aminoethylation reaction to introduce N-methylated aminoethylcysteine residues (FIG. 1B), thereby allowing the installation of methyl lysine analogues (MLAs) in histone proteins. This scheme provides a simple and affordable route to large quantities of specifically methylated histones. The MLA strategy is compatible with the installation of modifications in the nucleosome core including histone H3 Lys79—a modification that, even using state-of-the-art semi-synthesis strategies (Muralidharan, V. and Muir, T. W., *Nat*

*Methods*, 3:429-438 (2006)), would be extremely challenging to access. As shown below, we demonstrate that MLAs function similarly to their natural counterparts and are useful for the study of histone lysine methylation's influence on chromatin structure and function, among other uses.

II. Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y.), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses. In the discussion below, the abbreviation "Me" represents a methyl group, and the abbreviation "Ac" represents an acetyl group.

The terms "histones" or "histone proteins" are recognized by the skilled artisan as referring to the predominant class of proteins found in the chromatin of eukaryotic cells. Histones comprise 6 major proteins termed: H1, H2A, H2B, H3 and H4, which form a structure around which DNA is wound. Two each of the histone classes, H2A, H2B, H3 and H4, the so-called core histones, assemble to form one octameric nucleosome core particle by wrapping 146 base pairs of DNA around the protein spool in 1.65 left-handed super-helical turn. The linker histone, H1, binds the nucleosome, as well as, the entry and exit sites of the DNA, thus locking the DNA into place and allowing the formation of higher order structure. The most basic overall structure is the 10 nm fiber or beads on a string conformation. This structure entails the wrapping of DNA around nucleosomes with approximately 50 base pairs of DNA spaced between each nucleosome. See, e.g., Chromatin: Structure and Function, A. Wolffe (1998), Academic Press, London, for a review.

Histones are highly conserved proteins in eukaryotes, and the sequences of histones from many species are known in the art and are available from publicly accessible databases such as GenBank. Examples of representative GenBank accession numbers for histone sequences include: AAC61625, CAA47464, AAA63187, P62807, P62805, among many others that may be obtained through GenBank.

A "lysine residue analogue" refers to a chemical entity that can be introduced into a protein, for instance, a histone protein, to mimic the structure of the amino acid lysine. Such analogues can have substitutions of atoms normally found in lysine with other atoms (e.g., a sulfur atom substituted for a carbon atom), provided that the substitution results in a structure that is sterically and functionally similar to an unmodified lysine residue or a lysine residue modified by a post-translational modification such as methylation or acetylation. Generally, a "methylated" or "acetylated" lysine residue analogue refers to a chemical entity that can be introduced into a protein to mimic the structure of the amino acid lysine when methylated or acetylated at the epsilon amine of lysine. In one embodiment, a lysine residue analogue can be aminoethyl-cysteine.

A "modified lysine analogue" refers generally to a chemical entity that can be introduced into a protein, for instance, a histone protein, to mimic the structure of the amino acid lysine when modified by a post-translational modification. Examples of such post-translational modifications in the case of histones, include methylation and acetylation at the epsilon amino group of lysine.

The term "leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated nucleic acid encoding a histone protein is separated from open reading frames that flank the histone protein gene and encode proteins other than histones. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. An example in the present invention is aminoethylated cysteine, which functions as a modified lysine residue. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The terms "promoter" and "expression control sequence" are used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of monoclonal or polyclonal antibodies, any technique known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., Nature 348: 552-554 (1990); Marks et al., Biotechnology 10:779-783 (1992)).

An "immunogenic fragment" is one that elicits or modulates an immune response, preferably the composition induces or enhances an immune response in response to a particular histone protein or a portion thereof. Immune responses include humoral immune responses and cell-mediated immune responses, such as antibody production.

An "anti-histone" antibody is an antibody or antibody fragment that specifically binds a polypeptide encoded by a histone gene, cDNA, or a subsequence thereof including polypeptides encoded by a mutant histone gene, cDNA, or a subsequence thereof.

The term "immunoassay" is an assay that uses an antibody to specifically bind an antigen. The immunoassay is characterized by the use of specific binding properties of a particular antibody to isolate, target, detect, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Typically a specific or selective reaction will be at least twice background signal or noise and more typically more than 10 to 100 times background.

By "host cell" is meant a cell that contains an expression vector and supports the replication or expression of the expression vector. Host cells may be prokaryotic cells such as E. coli, or eukaryotic cells such as yeast, insect, amphibian, or mammalian cells such as CHO, HeLa and the like, e.g., cultured cells, explants, and cells in vivo.

III. Nucleic Acids Encoding Histone Proteins with Lysine to Cysteine Substitutions A. General Recombinant DNA Methods This invention relies on routine techniques in the field of recombinant genetics. Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, Tetrahedron Letts. 22:1859-1862 (1981), using an automated synthesizer, as described in Van Devanter et. al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

B. Site Directed Mutagenesis

Any of a number of methods are available to the skilled artisan for the substitution of one or more lysine residues in a histone protein with a cysteine residue. A variety of site-specific primer-directed mutagenesis and PCR-mediated mutagenesis methods are available and well-known in the art. See, e.g., Sambrook et al., supra; Ausubel et al., supra. For instance, the substitution of a particular lysine residue with a cysteine residue can be accomplished using methods such as site-directed mutagenesis (Carter et al., Nucl. Acids Res., 13:4331 (1986); Zoller et al., Nucl. Acids Res., 10:6487 (1987)), cassette mutagenesis (Wells et al., Gene, 34:315 (1985)), restriction selection mutagenesis (Wells et a., Philos. Trans. R. Soc. London SerA, 317:415 (1986)) or other techniques well known in the art. The mutagenized DNA is transformed into a host bacterium, and cultures of the transformed bacteria are plated and identified. The identification of colonies containing the mutation of interest may involve transfer of the DNA of selected transformants to a nitrocellulose filter or other membrane, and "lifts" may be hybridized with a labeled synthetic mutagenic primer at a temperature that permits hybridization of an exact match to the modified sequence but prevents hybridization with the original unmutagenized strand. Transformants that contain DNA that hybridizes with the probe are then cultured and used as a source of DNA for purposes such as overexpression of histone proteins carrying a particular lysine to cysteine substitution.

It will be apparent to the skilled artisan that site directed mutagenesis can also be used to substitute a selected subset or all of the normally occurring cysteine residues in a protein sequence with another amino acid residue, preferably one that does not have a side chain that can react with the alkylating agents of this invention. Another feature of the amino acid residue used to replace a naturally occurring cysteine residue is that the replacement amino acid residue does not affect the structure or function of the protein when the substitution is made. In one embodiment, all the normally occurring cysteines are replaced with other amino acids. However, if the cysteine residues are involved in, for instance, intra- or intermolecular disulfide bonds that are important for the maintenance of protein structure and function, such cysteine residues may preferably be left intact. In the case of histone proteins, generally, all the native cysteine residues will be replaced with other residues. In some embodiments, cysteine residues are changed to alanine or serine or other residues that are compatible with the maintenance of native structure and function of proteins, particularly histone proteins.

C. Expression of Histone Proteins in Prokaryotes and Eukaryotes

To obtain high level expression of a cloned gene, such as a DNA encoding a histone protein which has been engineered to have a specific lysine to cysteine substitution, one typically subclones the DNA into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing histone proteins are available in, e.g., E. coli, Bacillus sp., and Salmonella (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the histone protein encoding nucleic acid in host cells. A typical expression cassette thus contains a promoter operably linked to the nucleic acid sequence encoding the histone protein and signals required for efficient polyadenylation of the transcript, ribosome binding sites, and translation termination. The nucleic acid sequence encoding the histone protein may be linked to a cleavable signal peptide sequence to promote secretion of the encoded protein by the transformed cell if desired. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a histone protein encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of histone protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing a desired histone protein.

After the expression vector is introduced into the cells, the transfected cells are cultured under conditions favoring expression of the histone protein gene, which is recovered from the culture using standard techniques identified below.

D. Purification of Histone Proteins

Recombinant histone proteins may be purified from any suitable expression system to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al., supra; and Sambrook et al., supra).

1. Purification of Histone Proteins from Recombinant Bacteria

Recombinant proteins are expressed by transformed bacteria in large amounts, typically after promoter induction; but expression can be constitutive. Promoter induction with IPTG is a one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of inclusion bodies. For example, purification of inclusion bodies typically involves the extraction, separation and/or purification of inclusion bodies by disruption of bacterial cells, e.g., by incubation in a buffer of 50 mM Tris/HCl pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Histone proteins are separated from other bacterial proteins by standard separation techniques, e.g., with Ni-NTA agarose resin.

Alternatively, it is possible to purify histone proteins from bacteria periplasm. After lysis of the bacteria, when is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

2. Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

3. Column Chromatography

Histone proteins can also be separated from other proteins on the basis of their size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

E. Reaction of Recombinant Cysteine Containing Histone Proteins with Reagents to Install Methyl Lysine Analogs In general, any reagent that results in the conversion of a cysteine side chain of a histone protein to form a modified cysteine side chain with the structure —$CH_2$—S—$CH_2CH_2$—$NH(Y)_x$, where x can be 1, 2, or 3, and Y is either a methyl (Me) or acetyl (Ac) group, may be used. In an embodiment described in the Examples below, the recombinant cysteine containing histone proteins of the present invention are installed with methyl lysine analogs by reaction with compounds of the general formula: R—$CH_2CH_2$—$NH(Me)_x$, where R is a leaving group and x can be 1, 2, or 3. Such compounds are generally known as alkylating agents which result in the aminoethylation of a cysteine residue.

The leaving group R is capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxyamino, and the like. In general, a leaving group where the conjugate acid has a pKa lower than 1 may be used. In the case of the present invention, the nucleophile can be the —SH group on a cysteine side chain of a histone protein. The resulting modified histone comprises a cysteine residue with a side chain of the structure —S—$CH_2CH_2$—$NH(Y)_x$.

The chemical structures of some representative reagents of the type that may be used in the practice of this invention are shown in FIG. 9. The reagents shown in FIG. 9 can be synthesized by standard methods of organic chemistry known to the skilled artisan or may be purchased from a number of commercial vendors.

The skilled artisan will appreciate that the methods of the present invention can be used generally to introduce any type of modified lysine residues into a variety of proteins, of which, the introduction of methyl lysine and acetyl lysine into histone proteins are two exemplars.

Any standard reaction conditions known in the art that favor the alkylation of the free —SH group of cysteine with a —$CH_2CH_2$—$NH(Y)_x$ group may be used. In some instances, a reducing agent such as DTT is used to reduce the histone protein prior to and during the alkylation reaction. In some further instances, a denaturant, such as guanidinium chloride is used to partially denature the histone protein in order to better expose the cysteine residue undergoing alkylation.

F. Assays of Recombinant Histone Proteins

Functional assays of histone proteins are known in the art. Among these assays include the use of recombinant histone proteins, such as H3, to reconstitute histone octamers. The affinity of nucleosomes containing modified histones for binding to proteins such as DNA methyltransferases or SUZ12 can also be measured. Nucleosomes containing modified histone proteins may also be tested as substrates for the ATP-dependent remodeling complex hACF.

EXAMPLES

The following examples are offered to illustrate, but not to limit the claimed invention.

Example 1

Design of Methyl Lysine Analogues

Aminoethylcysteine has proven useful as an analogue of lysine for chemical rescue and cysteine mapping applications (Kenyon, G. L. and Bruice, T. W., *Methods Enzymol*, 47:407-430 (1977)). For example, a protein that contains a cysteine can be alkylated with an electrophillic ethylamine and the product (aminoethylcysteine, see FIG. 1A) can direct proteolytic cleavage using a lysine-directed protease such as trypsin (for early examples, see Raftery and Cole, 1966, and references therein).

Aminoethylcysteine is structurally and chemically similar to lysine; substituting the lysine γ-methylene with a sulfide causes only a slight lengthening of the side-chain (~0.28 Å) and the electron withdrawing effect of the thioether causes only a small increase in the acidity (~1.1 p$K_a$ unit) of the ammonium protons (see Gloss and Kirsch, 1995, and references therein). (See, also, FIG. 12.)

We have discovered that a related reaction would allow the introduction of analogues of methyl lysine into recombinant proteins. Indeed, the use of (2-bromoethyl)-timethylammonium bromide (3) was developed as a reagent to block cysteine residues (Itano, H. A. and Robinson, E. A., *J Biol Chem*, 247:4819-4824 (1972)), but to our knowledge has never been recognized as a useful analogue of trimethyl lysine. To develop other reagents that selectively alkylate cysteine residues to generate MLAs, we initially synthesized 2-iodoethyl amines (data not shown). While these reagents convert cysteine to the desired MLAs, we found that the commercially available (2-haloethyl) amines 1-3 (FIG. 1B) were similarly able to effect this conversion. While alkyl iodides are generally more reactive than alkyl chlorides and bromides, the high reactivity of (2-choloroethyl)-dimethylammonium chloride (2) can be attributed to an aziridinium intermediate formed under the reaction conditions (FIG. 1C). The formation of this reactive intermediate decouples the rate-limiting step (alkylation of the cysteine) from the leaving of the halide leaving group. A similar mechanism has recently been characterized for (2-bromoethyl) ammonium bromide (Hopkins, C. E. et al., *Arch Biochem Biophys*, 443:1-10 (2005)).

FIG. 9 shows the structures of some representative reagents that can be used to generate methyl and acetyl-lysine analogues of histones. FIG. 10 shows that alkylating agents 2-6 of FIG. 9 can be used to form methyl and acetyl-lysine analogues on a model cysteine-containing peptide. FIG. 11 shows that such reagents can be used to install both methyl and acetyl-lysine analogues into histone H3 protein, where lanes 2-4 show the incorporation of mono-, di-, and tri-methylated lysine analogues, respectively, and lane 5 shows the incorporation of an acetyl-lysine analogue.

The core nucleosome contains only a single conserved cysteine (H3 C110) that can be mutated to alanine without disrupting nucleosome function. Therefore a unique cysteine can be installed at any position (e.g. H4 K20C or H3 K79C in the background of a C110A mutation) and, upon treatment with an appropriate alkylating agent, the introduced cysteine can be converted into an analogue of monomethyl lysine, dimethyl lysine or trimethyl lysine. Given that N-substituted aminoethylcysteine residues are lysine (K) analogues derived from cysteine (C), we refer to them with the abbreviation $K_c$ and otherwise follow standard abbreviations (Turner, B. M., *Nat Struct Mol Biol*, 12:110-112 (2005)) for histone modifications (e.g., $K_c$9me3).

Example 2

Optimization of Conditions to Install Methyl Lysine Analogues into Proteins

Figure 2B:
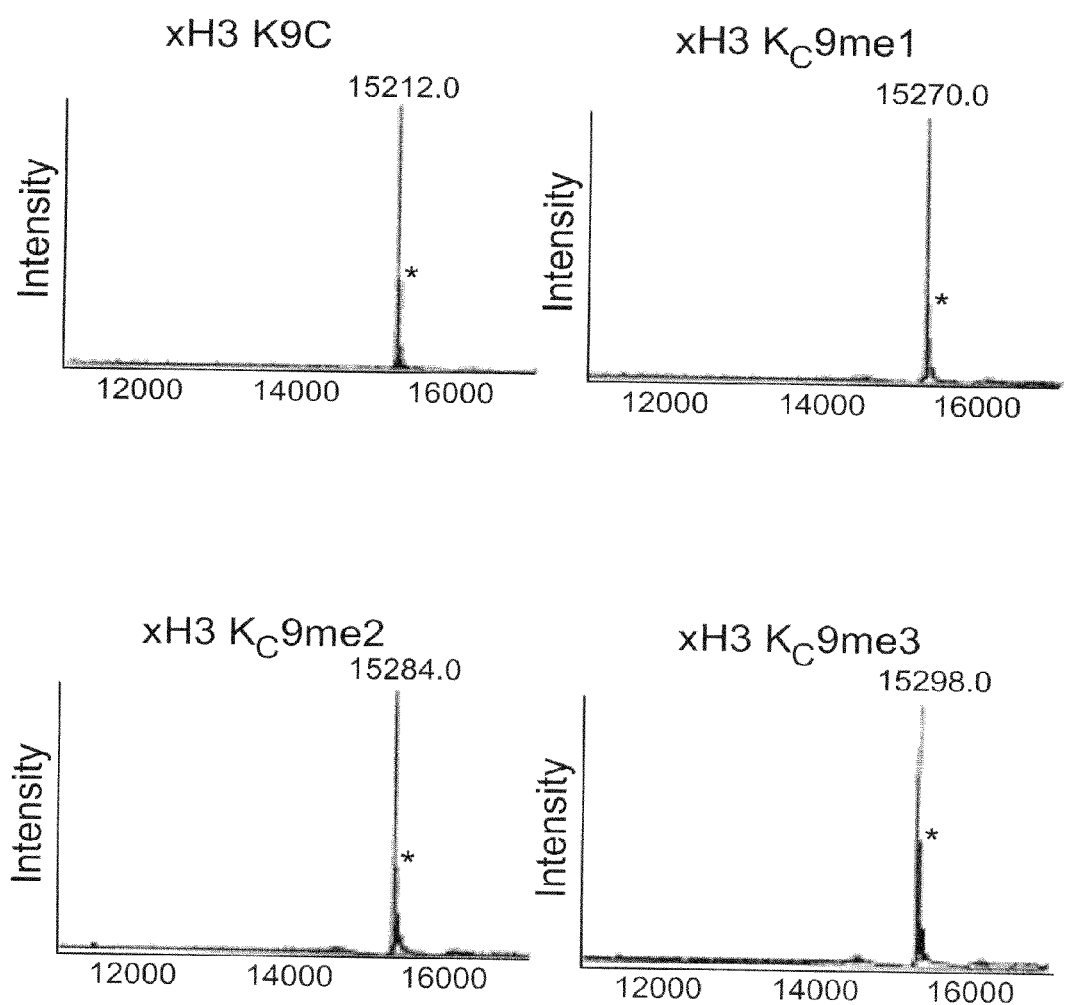

To determine whether the chemistry to install MLAs can produce homogeneous products for biochemical analysis, we used model cysteine-containing peptides to find conditions that promote specificity for cysteine alkylation over other nucleophilic side-chains, minimize variability caused by different sequence contexts and proceed with high conversion. Controlling the pH of the reaction was critical. At pH <7.5, cysteine residues are mostly protonated and the reactions proceeded sluggishly. At pH >8.5 side reactions were observed. However, reactions performed with reagents 1-3 using optimized buffer conditions, reaction time, temperature and concentrations of the alkylating agents afford good conversion (>90%) of cysteine to the desired MLAs in the context of a model peptide (FIG. 2A).

Extending these conditions to convert cysteine to the desired analogues in the context of full-length histones rather than peptides required increasing the concentration of denaturant (to increase the accessibility of cysteine residues installed at core positions, see FIG. 6A) and including free methionine to prevent low levels of oxidation observed in its absence (FIG. 6B). With these improvements, the reaction pH, concentration of alkylating agent, time and temperature were re-optimized to afford maximal conversion of cysteine residues to the desired MLAs (FIG. 6). By monitoring the reactions by ESI-oaTOF mass spectrometry, these conditions were found to be robust, leading to high conversion without excessive alkylation (shown for histone H3 K9C in FIG. 2B). Although a second peak at +42±1 Daltons was routinely observed in the product spectra, this peak was also observed in the starting material and is attributable to a mass spectrometry artifact; examination of the products on other mass spectrometers did not detect this contaminating species.

Comprehensive characterization of the proteins was carried out using Electron Capture Dissociation (ECD, Zubarev, R. A. et al., *Journal of the American Chemical Society*, 120: 3265-3266 (1998)) of the intact H3 Lys9-modified histones on a Fourier-transform ion cyclotron resonance mass spectrometer (FT-ICR). Most of the observed peaks in ECD spectra feature the N-terminal (c ions) and the C-terminal (z ions) fragmentation ions. The fragment ion ladder around residue 9 (e.g., $c_6^{2+}$, $c_7^{2+}$, $c_8^{2+}$, $c_9^{2+}$, $c_{10}^{3+}$ in FIG. 2C) indicates complete and homogenous incorporation of the desired modifications on residue 9. When comparing $K_c9me1$, $K_c9me2$ and $K_c9me3$ histones, the mass increment of the MLA containing ions (colored in magenta) equals the expected 14 amu, indicating they are mono-, di- and trimethylated, respectively (FIG. 2C).

These reaction conditions were found to be robust leading to clean installation of methyl-lysine analogues at every position that we have attempted to modify (see, for example, the modification of histones H3 K4C, H3 K36C, and H4 K20C shown in FIG. 7). Given the routine bacterial expression of large quantities of histone mutants (Luger, K. et al., *Methods Enzymol*, 304:3-19 (1999)) and the low cost of alkylating reagents 1-3, the MLA approach allows simple and economic access to large quantities of near-homogeneously (>90%) methylated histones.

Example 3

Functional Analysis of Methyl Lysine Analogues

Histone H3 methyl Lys9 analogues were used along with the other core histones to reconstitute histone octamers (FIG. 3A, Coomassie). Not only could Lys9 analogues be incorporated into histone ocatmers but also anti-sera raised against natural mono-, di- and trimethyl Lys9 specifically recognized the appropriate MLAs in western blots (FIG. 3A). The ability of anti-sera to recognize MLAs was not limited to H3 Lys9; similar results were achieved at other positions (H3 Lys4, H3 Lys36), including positions in the nucleosome core (H3 Lys79) and on histone H4 (H4 Lys20) as shown in FIGS. 3B and 3C. Despite their exquisite sensitivity to the presence or absence of a single methyl group, these antibody preparations react strongly with the appropriate MLAs, indicating that the MLA side-chains do not constitute a major perturbation to the natural methyl lysine epitopes, leading us to conclude that MLAs and natural methyl lysine residues are not easily distinguished in binding assays. In direct comparisons between peptides bearing K9me2 and $K_c9me2$, we found that the antibody recognition was still specific, but that $K_c9me2$ lead to a ~5-fold weaker signal in a dot blot assay relative to a K9me2 peptide (FIG. 8).

To further probe the functional similarity between natural methylated lysine residues and MLAs, we examined HP1 binding to Lys9 modifications. The structural perturbation caused by replacing lysine γ-methylene with a sulfide was addressed by modeling a $K_c9me2$ peptide into the crystal structure (Jacobs, S. A. and Khorasanizadeh, S., *Science*, 295:2080-2083 (2002)) of the HP1 chromodomain bound to a K9me2 peptide (FIG. 4A). The minimal differences observed in the model of the MLA peptide compared with the natural peptide suggest the analogue will bind similarly to HP1. To test this model, synthetic peptides were used as affinity reagents to enrich HP1α from a 293 nuclear extract (FIG. 4B). While a K9 peptide did not interact with HP1α, both a K9me2 peptide and a $K_c9me2$ peptide interacted strongly with HP1α. This result with model peptides raised the possibility that MLAs should also be functionally useful in the more complex case of MLA-bearing nucleosomes. Indeed, upon incorporation into biotinylated nucleosomes, $K_c9me2$ enhanced interactions between the modified nucleosome and HP1α relative to an unmodified nucleosome (FIG. 4C).

We next used mononucleosomes containing $K_c9me2$ to assay whether incorporation of MLA histones alters the affinity of nucleosomes for proteins in which histone methylation is not implicated in regulation of binding specificity. SUZ12 is important for nucleosome binding of the Polycomb Repressive Complex 2, histone methyltransferase complex (Nekrasov, M. et al., *EMBO Rep*, 6:348-353 (2005)). In affinity studies, SUZ12, did not distinguish between $K_c9me2$ and WT nucleosomes (FIG. 4D), indicating that incorporation of MLA histones does not non-specifically impair nucleosome accessibility and suggesting that methylation at Lys 9 does not regulate SUZ12's nucleosome binding activity.

Histone H3 Lys9 methylation is implicated in regulation of DNA methylation (Tamaru, H. et al., *Nat Genet*, 34:75-79 (2003)). We examined whether $K_c9me2$-containing nucleosomes bound the DNA methyltransferase DNMT1. This protein was not enriched when pulling down with either Lys9 modified or unmodified nucleosomes (FIG. 4E).

Although MLAs behave similarly to their natural counterparts in binding assays, the sensitivity of chemical catalysis to small changes in the structure of the reaction's transition state suggests that analogue function in an enzymatic assay is a more stringent criterion for similarity. To test analogue function in enzymatic reactions, peptides bearing either lysine or lysine analogues were examined as substrates for the Lys9-specific methyltransferase SUV39H1 (FIG. 5A). In this assay, a peptide bearing aminoethylcysteine was nearly as efficient a substrate for methylation as an unmodified lysine peptide. Furthermore, K9me2 and $K_c9me2$ substitutions both resulted in significantly lower SUV39H1 activity as was previously observed for a K9me2 peptide (Rea, S. et al., *Nature*, 406:593-599 (2000)). Consistent with this trend, a $K_c9me1$ peptide had an intermediate level of reactivity. We conclude that the lysine analogues behave in manner functionally similar to natural lysine residues even in the geometrically and chemically demanding context of an enzymatic reaction important for epigenetic regulation.

To test if nucleosomes prepared from histones with MLAs behave similarly to unmodified nucleosomes, salt dialysis was used to assemble histone octamers into end positioned nucleosomes with DNA encoding a strong positioning sequence (Lowary, P. T. and Widom, J., *J Mol Biol,* 276:19-42 (1998)). The resulting mononucleosomes were tested as substrates for the ATP-dependent remodeling complex hACF (FIG. 5B). In the presence of ATP, hACF was able to remodel nucleosomes from their end position to a centered position on the DNA (FIG. 5C). It is not surprising that the methyl Lys9 analogues have no apparent effect on the remodeling reaction; even complete removal of the H3 N-terminal tails does not substantially affect ACF activity (Eberharter, A. et al., *Embo J,* 20:3781-3788 (2001)). Nonetheless, similar remodeling of unmodified and MLA nucleosomes supports the conclusion that the chemical manipulation required to construct MLA histones does not have adverse effects on the histones, consistent with the clean installation of MLAs observed by mass spectrometry. Aside from the site of modification, nucleosomes with MLAs appear similar to unmodified nucleosomes in these assays.

While methylation at H3 K9 was not anticipated to affect the rates of ACF or ISWI-family nucleosome remodelers, H4 K20 is proximal to residues that interact with other members of the ISWI family (Clapier, C. R. et al., *Mol Cell Biol,* 21:875-883 (2001); Clapier, C. R. et al., *Nucleic Acids Res,* 30:649-655 (2002); Hamiche, A. et al., *Proc Natl Acad Sci USA,* 98:14316-14321 (2001)). To test if trimethyaltion at histone H4 residue 20 affects the rate of ACF mononucleosome remodeling, we assembled end-positioned nucleosomes with H4 $K_c$20me3 and compared their rate of ACF-remodeling with that of WT nucleosomes under conditions of excess and saturating ACF. In this assay, no significant differences were observed (data not shown). In efforts to uncover more subtle effects of $K_c$20me3 on remodeling, we repeated the remodeling assay and followed the progress of the reaction using a time course (FIG. 5D). No significant differences were observed between the remodeling of H4 $K_c$20me3 and WT nucleosomes. These data suggest that, despite the proximity of histone H4 K20 to residues that influence ACF activity, methylation at H4 K20 exerts its regulatory influence by a mechanism other than influencing the maximal rate of ACF nucleosome remodeling. The MLA strategy will be helpful for the investigation of other models connecting K20 methylation to transcriptional repression.

In addition to the potential regulatory roles exerted by post-translational modifications of histone tails, it has been suggested that modifications of residues in the globular domains in the core of the nucleosome may influence nucleosome stability or ATP-dependent nucleosome remodeling (Cosgrove, M. S. et al., *Nat Struct Mol Biol,* 11:1037-1043 (2004)). The MLA approach allows the generation of nucleosomes specifically methylated at core residues to test these hypotheses. For example, we generated nucleosomes specifically dimethylated at position 79 of histone H3 and tested whether or not this modification affects the rate of remodeling by ACF. End-positioned H3 $K_c$79me2 nucleosomes were remodeled with similar rates as WT nucleosomes (FIGS. 5D and E). In addition to demonstrating that $K_c$79me2 does not influence ACF remodeling under these conditions, these results underscore the utility of MLA histones to test nucleosome-level properties of methylated nucleosomes (such as remodeling), especially nucleosomes methylated at residues within the globular core of the nucleosome that are largely inaccessible by other techniques such as native chemical ligation.

Discussion

Understanding the impact of site-specific lysine mono-, di- and trimethylation on transcriptional regulation, development and tumorigenesis requires biochemical analysis of the effects of these modifications on chromatin structure and function. In some cases, the primary sequence context immediately surrounding the site of methylation appears sufficient to recapitulate a biochemical role for the modification. In such cases, including the binding interactions of H3 Lys9me to HP1α (Nakayama, J. et al., *Science,* 292:110-113 (2001)) and Lys27me to Polycomb (Fischle, W. et al., *Genes Dev,* 17:1870-1881 (2003); Min, J. et al., *Genes Dev,* 17:1823-1828 (2003)), peptides serve as useful models. In other contexts, however, it is likely that the role of the modification will require recognition elements present in the nucleosome but not necessarily nearby in the primary sequence. This is particularly likely for core modifications. Furthermore, for studies involving lysine modifications that directly affect nucleosome structure, mobility or stability, peptide models are not applicable. The need for the technology described here is made apparent by recent reports demonstrating H3 Lys4 methylation functions, at least in part, by directly recruiting remodeling factors (Wysocka, J. et al., *Nature,* 442:86-90 (2006)). Nucleosomes constructed using the MLA approach are useful for testing the regulatory influence of site-specific methylation on nucleosome-level biochemical activities as we have demonstrated by testing the effects of methylation at positions 9 and 79 of histone H3 and position 20 of histone H4 on nucleosome remodeling (see FIGS. 5C, D and E).

The MLA strategy described here provides an efficient and economical route to large quantities of recombinant methylated histones. The chemistry to install MLAs has been optimized to allow clean conversion of cysteine residues anywhere on the histones. The resulting analogues are stable except that, like methionine, they contain a thioether and are therefore susceptible to oxidation (i.e., sulfoxide formation). Standard precautions to avoid oxidizing conditions are sufficient to prevent these side reactions (FIG. 6B).

While MLAs differ from their natural counterparts by replacement of a methylene with a sulfide, we have found that, similar to previous reports using aminoethylcysteine, this perturbation causes minimal impact on function in binding and enzymatic assays. While the extent to which the MLAs mimic their natural counterparts will be context dependent, we found that antibodies generated against K9me1, K9me2, K9me3, K20me1, K4me3, K36me3 and K79me2 all demonstrated specific recognition of the appropriate analogues (FIG. 3), albeit in once case (i.e., K9me2) with approximately 5-fold lower activity (FIG. 8). Nonetheless, the success with antibodies and the results from other functional assays support the conclusion that MI-As serve as a general means to study lysine methylation. For example, here we examined the binding of candidate effector proteins and probed the influence of site-specific methylation on ATP-dependent nucleosome remodeling.

As the biochemical functions associated with each lysine methylation are elucidated, it will become increasingly important to study these modifications in combination. While the MLA strategy is not compatible with the installation of different degrees of methylation on the same histone subunit (e.g., H3 $K_c$9me3/$K_c$27me1), it is compatible with the installation of the same modification on different sites (e.g., H3 $K_c$4me3/$K_c$27me3) or different modifications on different subunits (e.g., H3 $K_c$27me3/H4 $K_c$20me1).

The biochemical analysis of the regulatory impact of specific histone lysine methylation marks has been largely limited to studying methylated peptides outside the context of nucleosomes. The MLA strategy facilitates the study of these important epigenetic marks in the context of nucleosomes. Ongoing studies include the use of MLAs to further investigate the role of lysine methylation in nucleosome remodeling studies, enzymatic assays, structural studies, compaction assays and in vitro transcription, particularly with respect to understanding repressive chromatin structures. Using the MLA strategy, proteins bearing specific methylation are straightforward to generate; their broad use will aid in studying the events downstream of lysine methylation, thereby expanding our understanding of the biochemical mechanisms underlying epigenetic regulation.

Example 5

Experimental Procedures

Histones, octamers and nucleosomes. Xenopus histones were expressed in *E. coli* and purified via gel filtration as previously described (Luger, K. et al., *J Mol Biol*, 272:301-311 (1997); Luger, K. et al., *Methods Enzymol*, 304:3-19 (1999)). All histone H3 constructs contain a C110A mutation including those labeled as WT here. Lys-to-Cys mutants constructed using Quikchange mutagenesis (Stratagene) according to the manufactures instructions. Histone octamers and nucleosomes were assembled according to previous reports (Luger, K. et al., *J Mol Biol*, 272:301-311 (1997); Luger, K. et al., *Methods Enzymol*, 304:3-19 (1999)). The DNA used for the assembly of mononucleosomes included the Widom 601 positioning sequence (Lowary, P. T. and Widom, J., *J Mol Biol*, 276:19-42 (1998)) with 49 bp of additional DNA and was constructed by PCR using biotinylated and Cy3-labeled primers. Nucleosomes constructed using MLA histones were purified and stored in the presence of 1 mM tris(2-carboxyethyl)phosphine hydrochloride (TCEP).

Peptide synthesis and alkylation. Peptides were synthesized using Fmoc protected amino acids according to standard methods. Fluoresceine-mPEG-GACR-OH, where F1 is Fluoresceine and mPEG is an ethylene glycol linker (building block: Fmoc-mini-PEG, Peptides International) and Biotin-mPEG-ARTKQTARXSTGGK-OH where X is either cysteine, lysine or dimethyl lysine as indicated. For peptide alkylations, HPLC purified peptides were dissolved in guanidinium chloride (10 µl, 8 M) and diluted with HEPES buffer (For $K_c$(me1) and $K_c$(me2): 85 µl, 1 M, pH 8; for $K_c$(me3) 88 µl, 1 M, pH 7.5) and DTT (2 µL of 1 M, dissolved immediately before use). The peptides were reduced for 1 h at 37° C. Alkylating agents were added as follows. For $K_c$(me1), (2-chloroethyl)-methylammonium chloride (1, Karl Industries Inc.) was added (10 µL of 3 M, dissolved immediately before use) and the reaction was allowed to proceed for 4 h. DTT was added (1 µl of 1 M) and after 30 min at rt, more alkylating agent was added (10 µL of 3 M). The reaction was allowed to proceed for 12 h. For $K_c$(me2), (2-chloroethyl)-dimethylammonium chloride (2, Aldrich) was added (10 µL of 1 M, dissolved immediately before use) and the reaction was allowed to proceed for 2 h. DTT was added (1 µl of 1 M) and, after 30 min at rt, additional 2 was added (10 µL of 1 M). The reaction was then allowed to proceed for 2 h. For $K_c$(me3), (2-bromoethyl)trimethylammonium bromide (3, Aldrich) was added as a solid (10 mg) and the reaction was heated to 50° C. in the dark. With occasional mixing, the solid dissolved slowly. After 2 h, DTT was added (1 µl of 1 M) and the reaction was allowed to proceed for another 2 h at 50° C. In all cases, the reactions were quenched with BME (5 µL, 14.2 M) and then analyzed or purified from the reaction mixture by analytical RP HPLC (A=$H_2O$ with 0.1% TFA; B=MeCN with 0.1% TFA). For HPLC of Fluoresceine-labeled peptides, absorbance was monitored at 430 nm. The identities of the products were confirmed by MALDI-TOF MS.

Installation of MLAs into full-length proteins. Lyophilized histones (5-10 mg) were dissolved in alkylation buffer (1 M HEPES pH 7.8, 4 M guanadinium chloride, 10 mM D/L-methionine, for $K_c$(me1) 900 µL; for $K_c$(me2) 930 µL; for $K_c$(me3) 980 µl,) and DTT was added (20 µL of 1 M, dissolved immediately before use). The histones were reduced for 1 at 37° C. Alkylating agents were added as follows. All reactions were performed in the dark. For $K_c$(me1), 1 was added (100 µL of 1 M, dissolved immediately before use) and the reaction was allowed to proceed for 4 h at room temperature. DTT was added (10 µl of 1 M) and the reaction was allowed to proceed for at least 10 h at room temperature. For $K_c$(me2), 2 was added (50 µL of 1 M, dissolved immediately before use) and the reaction was allowed to proceed for 2 h at rt. Then DTT was added (10 µl of 1 M), the reaction incubated at rt for 30 min, treated with additional 2 (50 µL, 1 M) and allowed to proceed for an additional 2 h rt. For $K_c$(me3), 3 was added as a solid (100 mg) and the reaction was heated to 50° C. With occasional mixing, the solid slowly dissolved. After 2.5 h, DTT was added (10 µl of 1 M) and the reaction was allowed to proceed for another 2.5 h at 50° C. In all cases, the reactions were quenched with BME (50 µL, 14.2 M) and then purified from the reaction mixture using PD-10 columns pre-equilibrated with BME/$H_2O$ (3 mM). The concentration of the eluant was quantified using a protein concentration assay (BioRad), the histones were aliquoted, lyophilized and stored as frozen pellets.

Mass Spectrometry. Mass spectrometry was performed on the following instruments. Peptides were analyzed on an ABI Voyager Elite MALDI-TOF using α-cyano-4-hydroxycinnamic acid as matrix. Routine analysis of MLA reactions was preformed using a Waters Micromass LCT premire. For more comprehensive analysis, the intact histones were analyzed on a 7-tesla hybrid linear ion trap (LTQ FT) mass spectrometer (Thermo Electron Corp., Palo Alto, Calif.) with a nano electrospray ion source at a concentration of ~5 pmole/ml. ECD spectra were acquired with a resolution of 100,000 and an isolation window of m/z 20. The activation and delay time in ECD were 5 ms and 8 ms. FT transients were accumulated, and ECD fragment ions were assigned using the Fragment Assignment by Visual Assistance (FAVA) algorithm in the MATLAB environment.

Nucleosome remodeling assays. Analysis of nucleosome remodeling by recombinant HACF was performed essentially as described (He, X. et al., *J Biol Chem*, 281:28636-28647 (2006)). Briefly, reactions (10 µL) were performed in 12% glycerol, 60 mM KCl, 12 mM HEPES, 4 mM Tris, 3 mM $MgCl_2$, 0.32 mM EDTA, 0.02% (Strohner, R. et al., *Nat Struct Mol Biol*, 12:683-690 (2005)). Briefly, reactions (10 µL) were performed in 12% glycerol, 60 mM KCl, 12 mM HEPES, 4 mM Tris, 3 mM $MgCl_2$, 0.32 mM EDTA, 0.02% NP-40 and 0.4 mg/mL FLAG peptide. Mononucleosomes (20 nM) assembled using Cy3 labeled DNA with the Widom 601 positioning sequence (Lowary, P. T. and Widom, J., *J Mol Biol*, 276:19-42 (1998)) and 49 bp additional DNA were incubated with recombinant hACF (25 nM). Reactions were started with Mg·ATP (2 mM) and incubated at rt for 30 min. before addition of stop buffer (2 µL, 0.8 mg/mL plasmid DNA, 115 mM ADP). The entire 12 µL reaction was analyzed by native PAGE (5% acrylamide, 0.5× Tris borate-EDTA gel, 2 h, 100 V) and the Cy3 fluorescence of the gel was visualized on an Amersham Typhoon 9400 variable mode imager at 580 nm. The time course experiments were performed similarly except the reactions were performed using subsaturating concentrations of ATP (4 µM·Mg-ATP, see Yang, J. G. et al., *Nat Struct Mol Biol*, 13:1078-1083 (2006)) and the reactions were incubated at 30° C.

Affinity studies. Nuclear extracts were prepared from 293 cells according to (Dignam, J. D. et al., *Nucleic Acids Res,* 11:1475-1489 (1983)) and then precleared with strepavidin-coated magnetic beads (1 mg beads per mL extract, Dynal M270). Biotinylated peptides (100 µg) or biotinylated nucleosomes (100 pmol) were diluted to 100 µL with wash buffer (100 mM KCl, 5 mM $MgCl_2$, 20 mM HEPES pH 7.6, 5% glycerol, 0.1 mg/mL BSA) and incubated with pre-washed strepavidin-coated magnetic beads (0.5 mg) for 30 min with mixing. The beads were washed 3× with wash buffer. The pre-cleared nuclear extract was added (20 µL) and the bead suspension was mixed for 1 h at 4° C. The beads were captured, the supernatant was aspirated and the beads rinsed 3× with wash buffer. The bound material was eluted with loading buffer, boiled for 5 min, resolved by denaturing PAGE (5-20%), transferred to a PVDF membrane and analyzed by western blot.

Co-immunoprecipitation and HMTase assays. Human SUV39H1 cDNA was cloned by PCR from HEK 293 cDNA, verified by sequencing, and subsequently fused to a GFP tag in the pEGFP-C3 vector (Clontech). The plasmid was transfected into HEK 293 cells ($5\times10^6$/10-cm plate) using FuGENE6 (Roche Applied Science) according to manufacturer's conditions. Forty-eight hours after transfection, HEK 293 cells were processed for co-immunoprecipitation as described (Chu, F. et al., *Mol Cell Proteomics,* 5:194-203 (2006)). The immunoprecipitation reactions were performed at 4° C. overnight. The resulting immunoprecipitates were then subjected to HMTase assays essentially as described (Rea, S. et al., *Nature,* 406:593-599 (2000)). S-Adenosyl-L-(methyl-$^3$H) Methionine (74.0 Ci/nmol. Amersham) was used as the methyl donor and 4 µg of biotinylated N-terminal peptides were used as the substrate. After the HMTase assay, peptides were spotted onto SAM2 Biotin Capture Membranes (Promega), washed, and subjected to scintillation counting as described (Lindroth, A. M. et al., *Embo J,* 23:4286-4296 (2004)).

Antibodies. Antibodies used include: anti-HP1α, (Upstate, mouse monoclonal, 05-689), anti-trimethyl-histone H3 Lys27 (Upstate, mouse ascites, 05-851), anti-DNMT1 (Abcam, mouse monoclonal, ab13537), anti-GFP (Abcam, rabbit polyclonal, ab290), anti-monomethyl-histone H3 Lys9 (Upstate, rabbit polyclonal, 07-395), anti-dimethyl-histone H3 Lys9 (Upstate, rabbit polyclonal, 07-212), anti-trimethyl-histone H3 Lys9 (Upstate, rabbit polyclonal, 07-442), anti-monomethyl H4 Lys20 (Upstate, rabbit monoclonal, NL314), anti-trimethyl H3 Lys4 (Abcam, rabbit polyclonal, ab8580), anti-trimethyl H3 Lys36 (Abcam, rabbit polyclonal, ab9050), anti-dimethyl H3 Lys79 (Abcam, rabbit polyclonal, ab3594) and anti-SUZ12 (Upstate, rabbit polyclonal, 07-379).

Buffer for alkylation reactions. To make 100 mL of alkylation buffer, HEPES (6.46 g), HEPES sodium salt (18.98 g) and D/L-Methionine (149 mg) were combined in a beaker and the volume was increased to 55 mL with water. Guanidine hydrochloride (38.21 g) was slowly added while stirring. Water was added to 100 mL and the resulting solution was filtered.

It is understood that the examples and embodiments described herein are for illustrative purposes only and that various modifications or changes in light thereof will be suggested to persons skilled in the art and are to be included within the spirit and purview of this application and scope of the appended claims. All publications, accession numbers, patents, and patent applications cited herein are hereby incorporated by reference in their entirety for all purposes.

What is claimed is:

1. A method of introducing a site specific mono-, di, or tri-methylated lysine residue analogue into a histone H3 or H4 protein comprising the steps of:
   (a) mutating the cysteine residues in the native sequence of the histone protein to a different amino acid residue;
   (b) mutating at least one lysine residue in the amino acid sequence of the histone protein to a cysteine residue to generate a cysteine containing protein; and
   (c) contacting the cysteine containing protein with a compound of the structure: R—CH2CH2-NH(Me)x, wherein R is a leaving group and x is 1, 2, or 3, thereby introducing a site specific mono-, di, or tri-methylated lysine residue analogue into a histone protein.

2. The method of claim 1, wherein the different amino acid residue is alanine.

3. The method of claim 1, wherein R is a halide.

4. The method of claim 3, wherein the halide is Cl, Br, or I.

5. The method of claim 1, wherein R is mesylate or tosylate.

6. The method of claim 1, wherein the specific lysine residue is K4, K9, K14, K27, K36, or K79 of histone H3.

7. The method of claim 1, wherein the specific lysine residue is K5, KS, K12, K16, or K20 of histone H4.

8. The method of claim 1, wherein the cysteine containing protein is treated with a reducing agent prior to step (c).

9. The method of claim 8, wherein the reducing agent is DTT.

10. An isolated histone H3 or H4 protein comprising a lysine to cysteine substitution, wherein the substituted cysteine comprises the side chain structure —S—CH2CH2-NH(Me)x, wherein x is 1, 2, or 3.

11. The isolated histone protein of claim 10, wherein the lysine to cysteine substitution is K4C, K9C, K14C, K27C, K36C, or K79C of histone H3.

12. The isolated histone protein of claim 10, wherein the lysine to cysteine substitution is K5C, K8C, K12C, K16C, or K20C of histone H4.

13. An isolated histone H3 or H4 protein comprising site specific mono-, di, or tri-methylated lysine residue analogues derived by a process comprising the steps of:
   (a) mutating the cysteine residues in the native sequence of the H3 histone protein to alanine;
   (b) mutating at least one lysine residue in the sequence of the H3 protein to a cysteine residue to generate a cysteine containing protein; and
   (c) contacting the cysteine containing protein with a compound of the structure: RCH2CH2-NH(Me)x, wherein R is a leaving group and x is 1, 2, or 3.

14. The isolated histone protein of claim 13, wherein R is a halide.

15. The isolated histone protein of claim 14, wherein the halide is Cl, Br, or I.

16. The method of claim 13, wherein R is mesylate or tosylate.

17. The isolated histone protein of claim 13, wherein the histone protein is histone H3 or H4.

18. The isolated histone protein of claim 13, wherein the specific lysine residue is K4, K9, K14, K27, K36, or K79 of histone H3.

19. The isolated histone protein of claim 13, wherein the specific lysine residue is K5, K8, K12, K16, or K20 of histone H4.

20. A method for assaying the effect of methylation of at least one lysine residue on a histone protein on the histone H3 or H4 protein's activity comprising the steps of:
   (a) mutating the cysteine residues in the native sequence of the histone H3 protein to alanine;

(b) mutating at least one lysine residue in the sequence of the histone protein to a cysteine residue to generate a cysteine containing histone protein;

(c) contacting the cysteine containing histone protein with a compound of the structure: R—CH2CH2-NH(Me)x, wherein R is a leaving group and x is 1, 2, or 3 to generate a methylated protein; and (d) comparing the activity of the methylated histone protein with the histone protein without the mutation or with a protein derived after step (c) in which x is 0, thereby assaying the effect of methylation of at least one lysine residue on the histone protein's activity.

21. The method of claim 20, wherein the assaying comprises measuring octomer reconstitution.

22. The method of claim 20, wherein the assaying comprises measuring nucleosome remodeling.

23. The isolated histone protein of claim 10, wherein the histone protein further comprises substitution of the cysteine residues in the native sequence of the histone protein to a different amino acid residue.

* * * * *